(12) United States Patent
Medoff et al.

(10) Patent No.: US 10,039,579 B2
(45) Date of Patent: Aug. 7, 2018

(54) SYSTEM AND METHOD FOR TREATING BONE FRACTURES

(71) Applicant: TriMed, Incorporated, Santa Clarita, CA (US)

(72) Inventors: Robert Medoff, Kailua, HI (US); Jesse B. Jupiter, Weston, MA (US)

(73) Assignee: TriMed, Inc., Santa Clarita, CA (US)

( * ) Notice: Subject to any disclaimer, the term of this patent is extended or adjusted under 35 U.S.C. 154(b) by 191 days.

(21) Appl. No.: 14/383,599

(22) PCT Filed: Dec. 19, 2012

(86) PCT No.: PCT/US2012/070649
§ 371 (c)(1),
(2) Date: Sep. 8, 2014

(87) PCT Pub. No.: WO2013/133886
PCT Pub. Date: Sep. 12, 2013

(65) Prior Publication Data
US 2015/0112343 A1    Apr. 23, 2015

Related U.S. Application Data

(60) Provisional application No. 61/608,315, filed on Mar. 8, 2012.

(51) Int. Cl.
*A61B 17/56* (2006.01)
*A61B 17/72* (2006.01)
(Continued)

(52) U.S. Cl.
CPC .......... *A61B 17/72* (2013.01); *A61B 17/1725* (2013.01); *A61B 17/683* (2013.01);
(Continued)

(58) Field of Classification Search
CPC ..... A61B 17/72; A61B 17/80; A61B 17/7291; A61B 2017/564; A61B 17/7241
(Continued)

(56) References Cited

U.S. PATENT DOCUMENTS

| | | | | |
|---|---|---|---|---|
| 3,709,218 A | * | 1/1973 | Halloran | A61B 17/72 606/64 |
| 5,658,288 A | * | 8/1997 | Kim | A61B 17/725 606/308 |
| 5,659,288 A | | 8/1997 | Kim | |
| 7,179,259 B1 | | 2/2007 | Gibbs | |
| 7,563,263 B2 | * | 7/2009 | Orbay | A61B 17/7233 606/62 |
| 2005/0165400 A1 | * | 7/2005 | Fernandez | A61B 17/8057 606/281 |
| 2005/0240187 A1 | * | 10/2005 | Huebner | A61B 17/80 606/71 |
| 2008/0177395 A1 | | 7/2008 | Stinnette | |
| 2008/0300637 A1 | * | 12/2008 | Austin | A61B 17/74 606/290 |
| 2009/0177240 A1 | * | 7/2009 | Perez | A61B 17/7233 606/86 R |
| 2009/0292320 A1 | | 11/2009 | Mullaney et al. | |

(Continued)

OTHER PUBLICATIONS

Extended European Search Report dated Oct. 13, 2015 in European Patent Application No. 12 87 0685.

*Primary Examiner* — Eduardo C Robert
*Assistant Examiner* — Tara R Carter
(74) *Attorney, Agent, or Firm* — Wood, Phillips, Katz, Clark & Mortimer

(57) ABSTRACT

A system and method for treating a fracture of a bone that produces first and second bone parts separated by a fracture line. A first implant has a first body. A second implant has a second body, A first elongate component can be directed through the bone to cooperate with each of the first and second bodies so that the first and second bodies and first component together act to maintain the first and second bone parts in a desired set relationship. The first component has a lengthwise axis and cooperates with the first body so that the operatively positioned first component is stabilized by the first body in a direction that is transverse to the lengthwise axis of the first component. The first component cooperates with the second body so that the first component is stabilized by the operatively positioned second body.

47 Claims, 26 Drawing Sheets

(51) Int. Cl.
  *A61B 17/17* (2006.01)
  *A61B 17/68* (2006.01)
  *A61B 17/80* (2006.01)
  *A61B 17/16* (2006.01)
  *A61B 17/86* (2006.01)

(52) U.S. Cl.
  CPC ........ *A61B 17/7233* (2013.01); *A61B 17/809* (2013.01); *A61B 17/8061* (2013.01); *A61B 17/863* (2013.01); *A61B 17/1675* (2013.01); *A61B 17/1684* (2013.01); *A61B 17/1697* (2013.01); *A61B 17/1764* (2013.01); *A61B 17/1778* (2016.11); *A61B 17/86* (2013.01)

(58) Field of Classification Search
  USPC .......................... 606/62–68, 70, 71, 280–299
  See application file for complete search history.

(56) References Cited

U.S. PATENT DOCUMENTS

| | | | |
|---|---|---|---|
| 2009/0312802 A1 | 12/2009 | DaSilva | |
| 2010/0318086 A1* | 12/2010 | Winemaker | A61B 17/683 606/70 |
| 2011/0166573 A1* | 7/2011 | Wenk | A61B 17/80 606/71 |
| 2013/0096559 A1* | 4/2013 | Katrana | A61B 17/8061 606/71 |

* cited by examiner

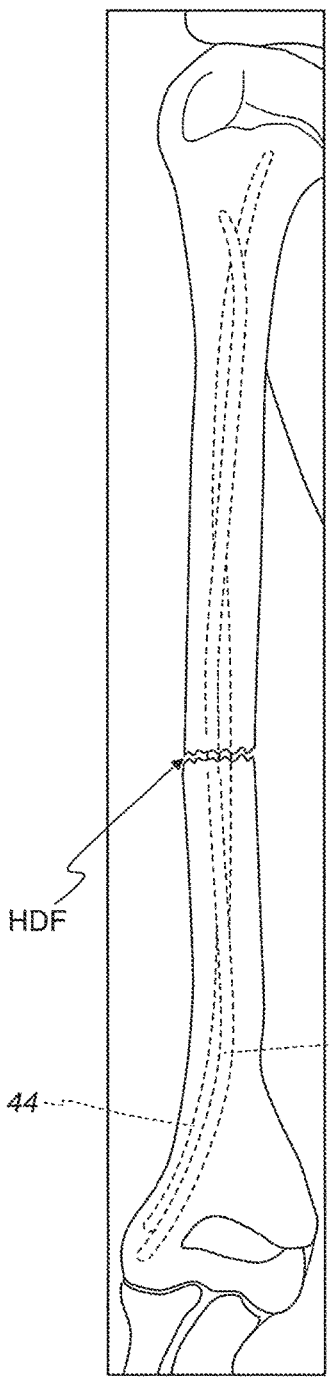
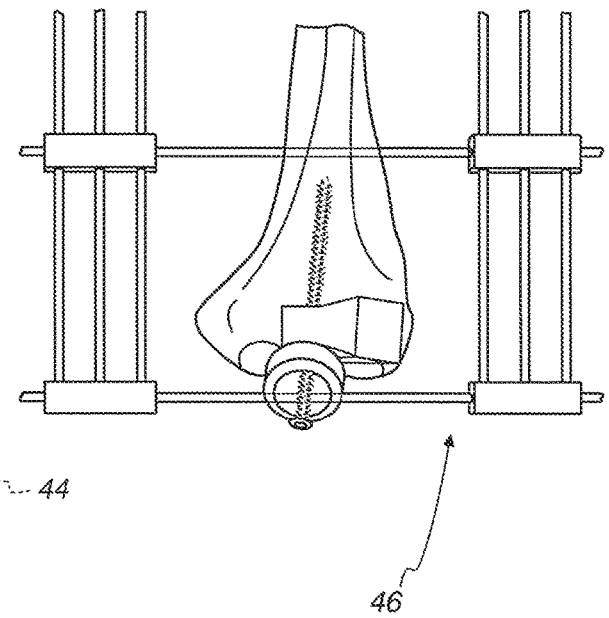
Fig. 12
(Prior Art)
Fig. 13
(Prior Art)

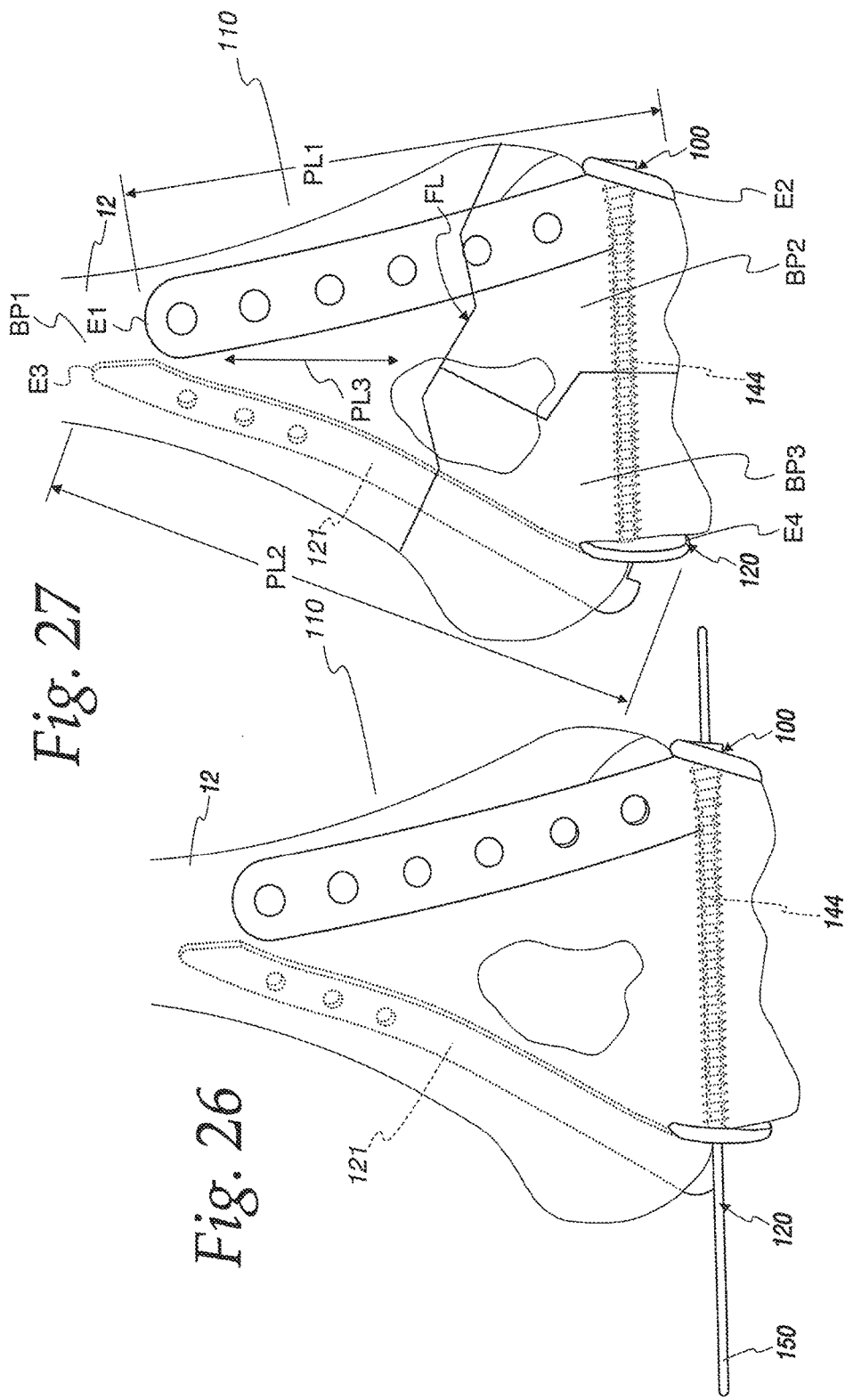

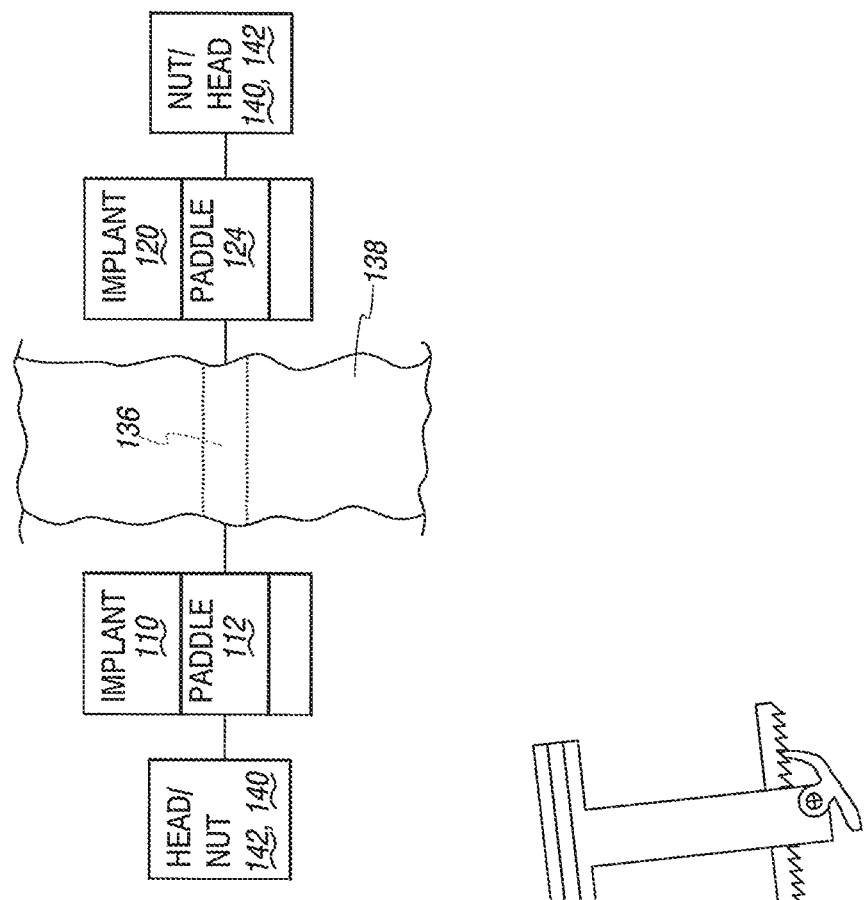
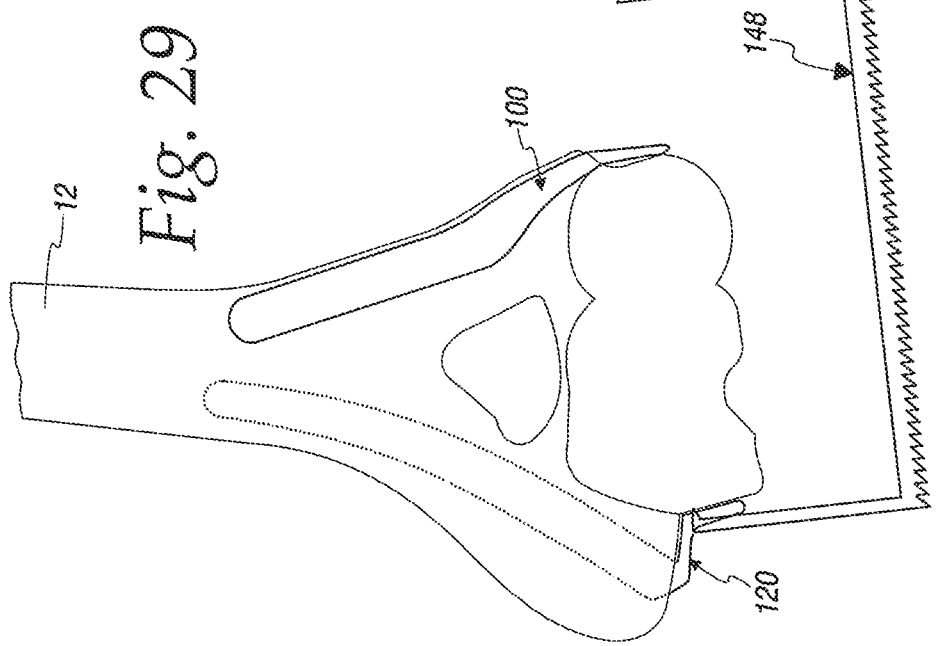

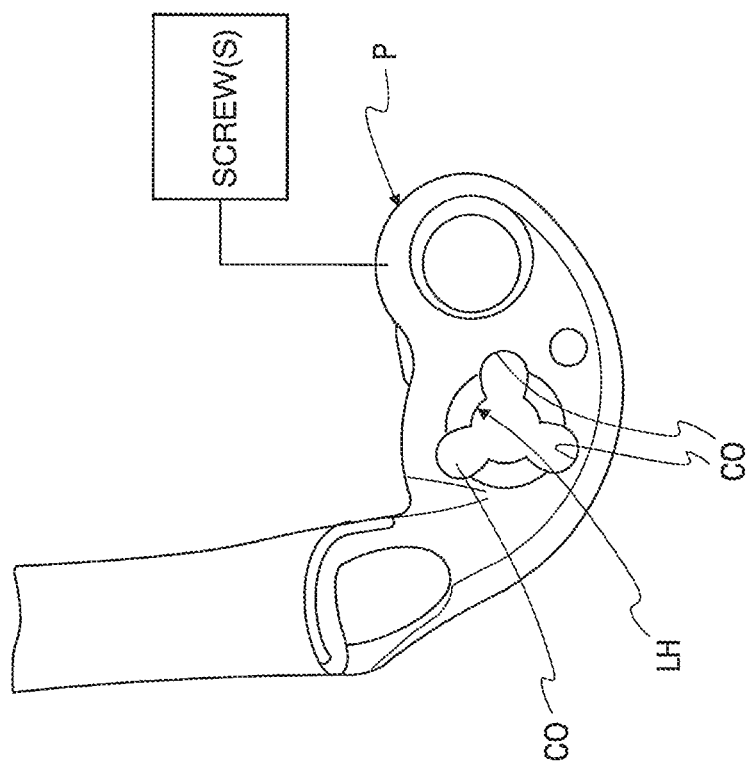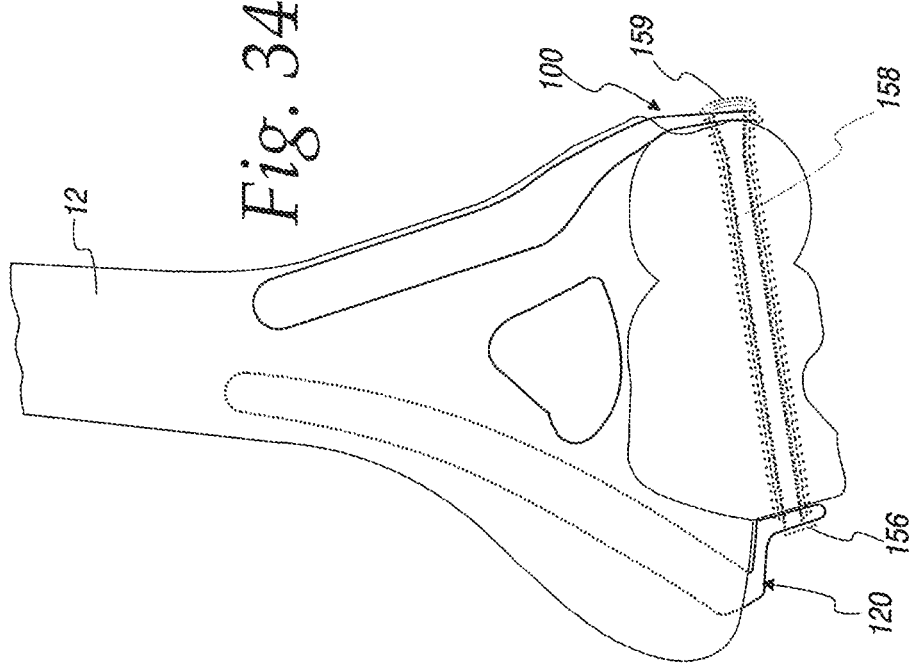

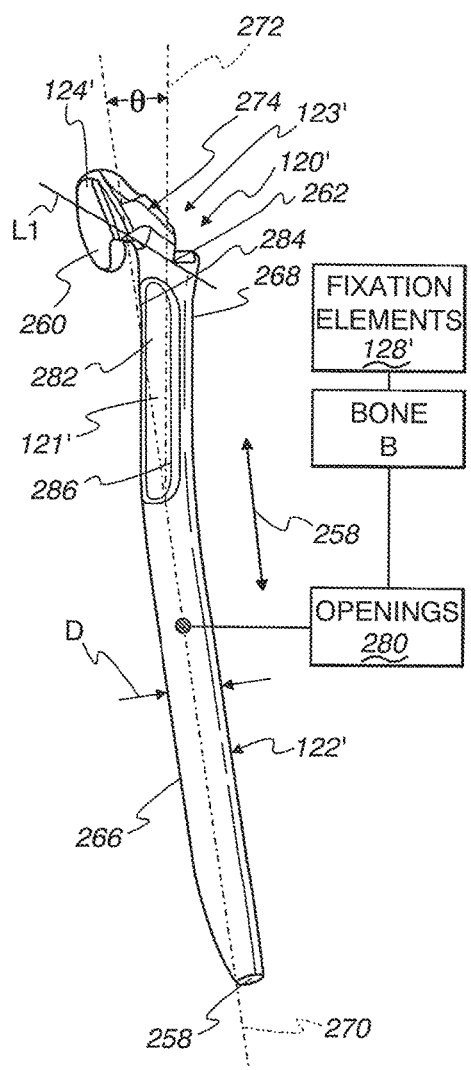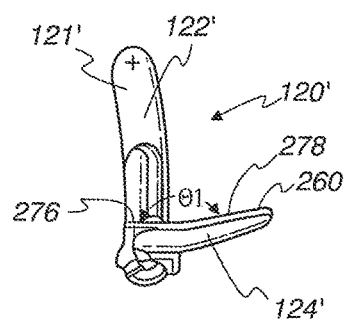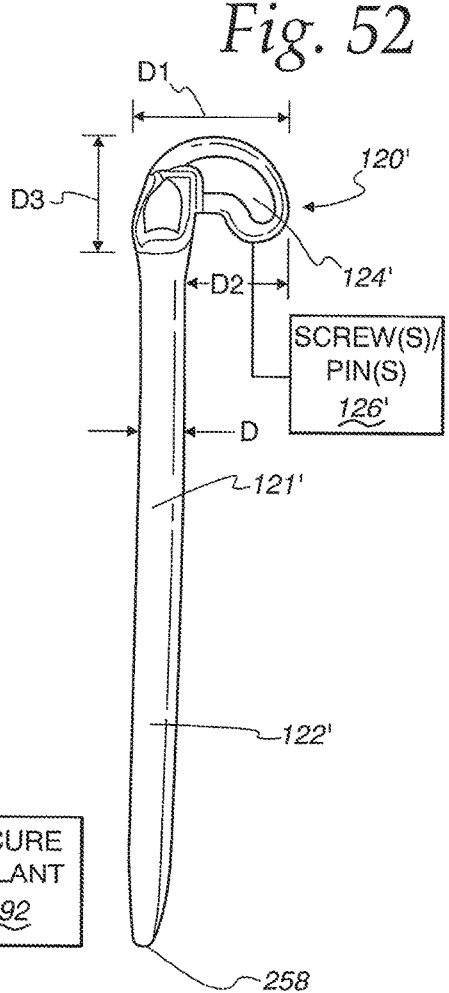
Fig. 50
Fig. 51
Fig. 52
Fig. 53

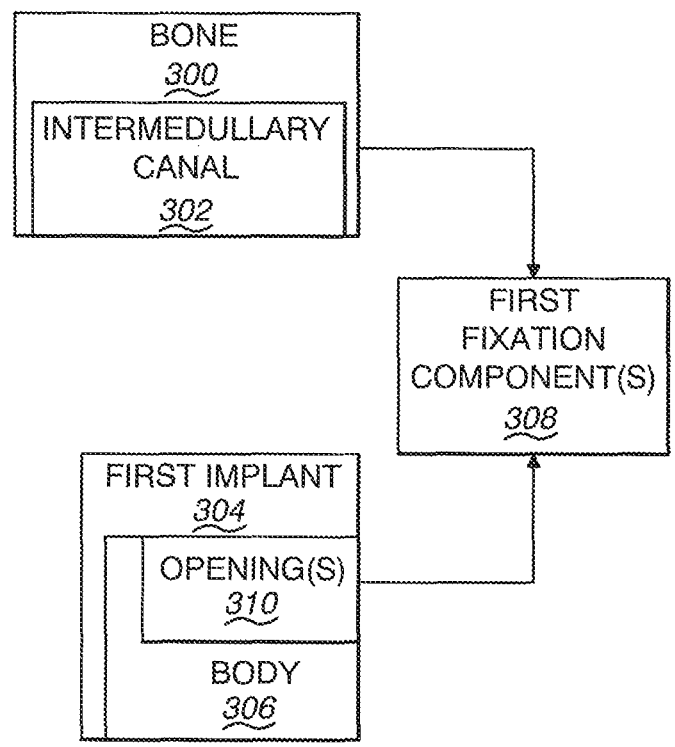
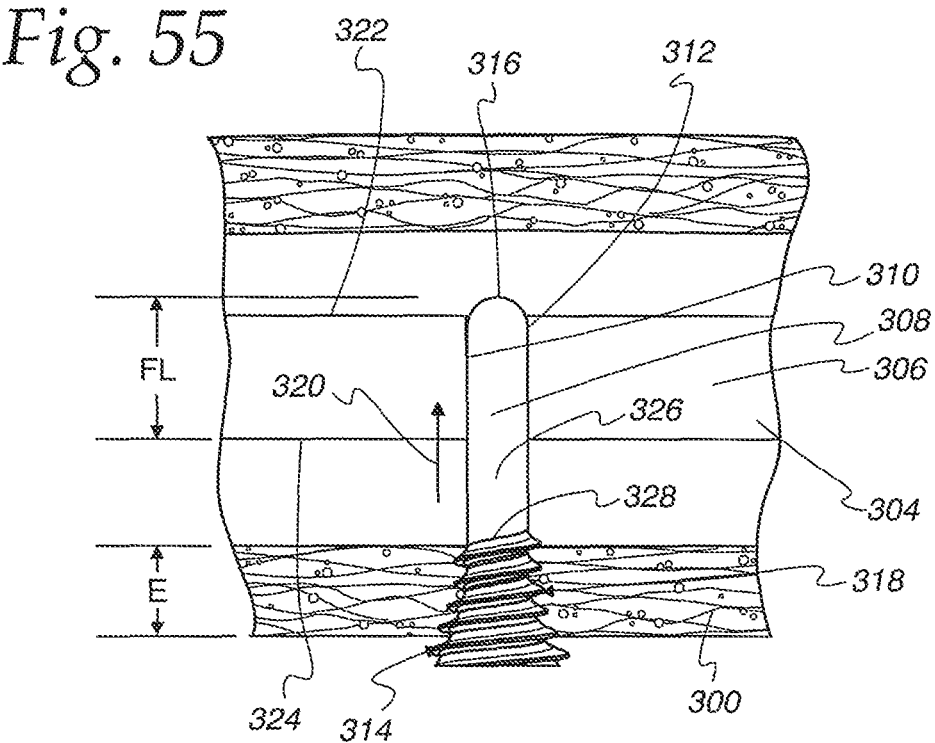

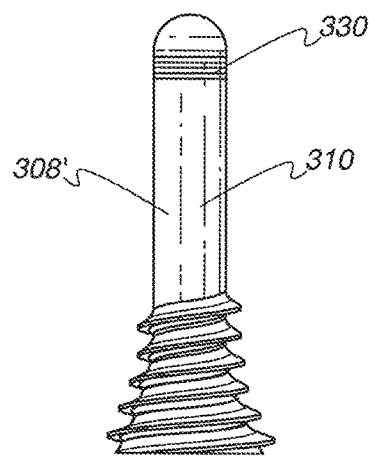
Fig. 56
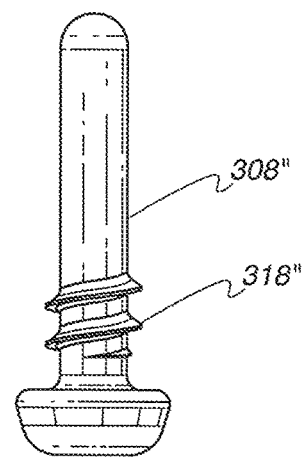
Fig. 57
Fig. 58
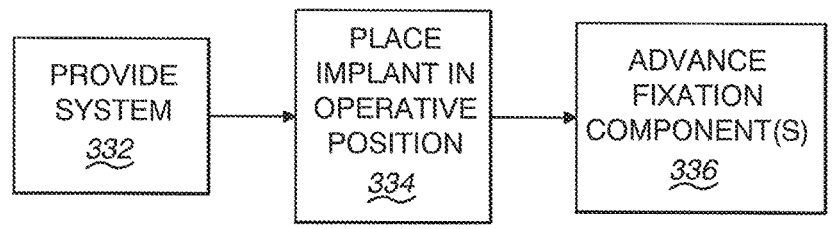

SYSTEM AND METHOD FOR TREATING BONE FRACTURES

BACKGROUND OF THE INVENTION

Field of the Invention

This invention relates to bone fractures and, more particularly, to a method and apparatus for treating bone fractures utilizing cooperating implants.

Background Art

As seen in FIGS. 1 and 2, the human elbow joint at 10 is essentially a hinge joint, formed from the articulation of the lower portion of the distal humerus 12 with the proximal portions of the two bones of the forearm—the radius 14 and ulna 16. Where these three bones come in contact with each other, the surface of the bone is covered with articular cartilage which provides a slippery joint lining that allows gliding and motion of the bone on one side of the joint against the bone on the other side of the joint. Anatomically, the articular surface of the distal humerus 12 is formed into two condyles that act like curved runners to allow tracking of the articular surface of the corresponding proximal end of each forearm bone 14, 16. The medial condyle of the distal humerus 12 articulates with the olecranon (the proximal articulating surface of the ulna 16) and the lateral condyle of the distal humerus articulates with the radial head (the proximal articulating surface of the radius 14). Because of this anatomical arrangement, motion between the humerus 12 and the proximal portion of the two forearm bones 14, 16 is limited to simple flexion and extension.

The medial condyle is trochlear or hourglass in shape and is called the trochlea. The trochlea conforms to the C-shaped structure of the olecranon (proximal ulna) and allows simple flexion and extension. The anterior end of the C-shaped proximal ulna at 18 is called the coronoid process which recesses into a corresponding depression on the anterior surface of the distal humerus at 20, called the coronoid fossa, with extremes of elbow flexion. The posterior end of the C-shaped proximal ulna at 22 is called the olecranon process. It recesses into a corresponding depression at 24 on the posterior surface of the distal humerus 12 called the olecranon fossa with extension. Because the coronoid fossa 20 and the olecranon fossa 24 are diametrically positioned on the anterior and posterior surfaces of the distal humerus 12 directly proximal to the articular surface, this central triangular portion of the bone can be quite thin. Occasionally, this portion of the bone is actually absent.

In contrast to the medial condyle at 26, the lateral condyle at 28 is basically spherical in shape and called the capitellum. It conforms with the cup-shaped end of the radial head (proximal radius) 30 and allows gliding of the radial head 30 over the capitellum 28 during simple flexion and extension of the elbow. In addition, it also allows the radial head 30 to rotate on the capitellum 28 with movement of the forearm into pronation and supination.

Proximal to the articular condyles of the distal humerus 12, the distal end of the humerus has bony prominences on both the medial and lateral aspects of the bone. These prominences are called the medial epicondyle 32 and the lateral epicondyle 34, respectively. Each of these epicondyles functions as an anchor point for attachment of the strong muscles of the forearm, with the strong flexor and pronator group of muscles attached to the medial epicondyle and the strong extensor and supinator group of muscles attached to the lateral epicondyle 34. Because of the combination of the bony pillars that make up the medial and lateral sides of the distal humerus 12 with the thin central area formed from the olecranon and coronoid fossas, the distal humerus 12 structurally is essentially triangular, with medial and lateral columns of bone that are connected distally with a horizontal osseous pillar made up by the combination of the capitellum 28 and trochlea 36.

Fractures of the distal humerus 12 can be simple or complicated. Reference is made to FIGS. 3-8 which show different types of fractures, successively at F1, F2, F3, F4, F5, F6. Supracondylar fractures describe fractures that extend across the bone with a fracture line that typically crosses the region of the thin olecranon and coronoid fossas. Supracondylar fractures may be simple with a single transverse fracture line, comminuted with intermediate segments that extend up the shaft, or involve fragmentation of the articular surface, such as T-condylar fractures, as seen in FIGS. 7 and 8. In contrast, the term condylar fractures describe fractures that involve only the medial or lateral condyle. Lateral condylar fractures are shown in FIGS. 3 and 4 with medial condylar fractures shown in FIGS. 5 and 6.

Treatment of condylar and supracondylar fractures can be challenging. Because large bending forces are generated by the long lever arms of the humerus and forearm, closed methods of treatment such as simple cast immobilization often are ineffective. Interfragmentary pins 38, as seen in FIGS. 9a-9d have been used to supplement fixation, but this fixation is often tenuous and poses difficulties to obtain and hold an accurate reduction (restoration of the joint anatomy). These pins 38 are shown in FIGS. 9a-9d on bone parts produced by a supracondylar fracture, in addition, since pin fixation lacks structural rigidity, treatment typically requires prolonged immobilization and can often result in permanent stiffness and dysfunction of the joint.

In an effort to overcome these problems, open reduction and internal fixation have been used in an attempt to achieve anatomic restoration of the joint that is rigid enough to allow early motion. Typically, open reduction internal fixation uses standard pins, screws and plates or combinations of these components. In addition to the objective of restoration of joint anatomy, open reduction internal fixation should avoid further morbidity and complications from the internal fixation itself. Unfortunately, existing methods of internal fixation often fall far short of achieving these goals.

As seen in FIG. 10, use of medial plates MP, lateral plates LP, and screws S is the most common form of internal fixation. With this method, the fracture is reduced and temporarily held in place while plates LP, MP are applied to the bone surface and secured with screws S. Because the plates. LP, MP are on the surface of the bone, they are subject to the large bending moments alluded to previously. As a result, the plates LP, MP are usually quite thick in order to prevent breakage. Because of this bulk, application on a small bone is difficult and it is extremely difficult to bend the plates LP, MP to fit the contour and shape of a particular bone. In addition, thick plates also have the disadvantage of causing significant soft tissue irritation and often require removal.

Because bending forces on these devices are high, plates require bone screws that are large and strong enough to handle the applied loads. However, these larger screw sizes are often too large for the relatively small size of the distal fragments, resulting in problems that include tenuous or failed fixation, iatrogenic fragmentation of the bone fragment through the relatively large hole that is needed for placement of the screw, and irritation of the soft tissues from bulky hardware. Furthermore, fixation with standard plates is completely dependent on the quality of the screw thread purchase in the bone; severe osteoporosis or highly comminuted fractures result in poor thread purchase and significantly increase the risk of failure. Fragments are typically small and often with a large part of the bone surface covered with articular cartilage (plates/screws cannot be applied to the surface of the joint) leaving little to no room for plate application. Plates cannot interfere or cross in the coronoid or olecranon fossa, resulting in further reduction of the area available for plate application.

Plates and screws are subject to large bending moments from cantilever bending as load is applied to the bone. Plates fixed with standard screws are completely dependent on thread purchase in the bone in order to achieve structural rigidity. Unfortunately, often the size and quality of the soft cancellous bone in the supracondylar fragments is insufficient to provide this strength, resulting in screw cutout, failure, or loss of reduction.

Locking screws (i.e., screws that lock into the plate by threading into the plate) tend to reduce some of the failures related to poor thread purchase. However, since locking screws require a threaded hole in the plate, this design increases the bulk of the plate further. In addition, since locking screws are still subject to the same cantilever bending loads, the use of locking screws does not eliminate the need for relatively large screws for strength. Large screws introduce the related problems of soft tissue irritation, bulky hardware, and iatrogenic fracture from placement of large screw holes in small fragments.

The many variations on basic plate and screw design are a reflection on the multiple attempts to address these issues with supracondylar fracture fixation. Most changes simply involve varying the location of plate application or variation of the shape of the plate to match the surface bone contour. All share the common problem faced by the conflicting need to use a large enough plate to handle the load while avoiding the problems associated with bulk and screw purchase and strength in the distal fragments. In all of these designs, the generation of large cantilever bending loads can create large stresses on both implants and the bone implant interface.

For instance, one known approach is to use a shaped plate applied to the posterior surface with arms that extend down the medial and lateral column. This plate design is unable to address fixation of very distal articular fragments since screw fixation of such fragments must enter from the non-articular surfaces directly from the medial or lateral side and not posteriorly. Also, these plates are at a mechanical disadvantage and subject to very large bending moments, since the primary arc of motion in flexion and extension occurs in a plane that is perpendicular to the plate surface. Unless the plate is quite thick, it will bend or break.

Another approach is to apply plates on the medial column, the lateral columns, or both, as in FIG. 10. These plates are oriented in a plane that is parallel to the arc of motion. Since these plates are subject to large medial/lateral bending loads, they still need to be thick enough to resist breakage. On the other hand, since they lie directly on the medial and lateral surfaces, they are relatively subcutaneous and prone to cause soft tissue irritation. Another problem with medial/lateral plate application is that the medial and lateral sides of the bone have a complex shape, making it difficult to design and manufacture a plate that matches the complex bone morphology.

Another problem with medial or lateral plates is that they have to be applied over the medial or lateral epicondyle respectively. Unfortunately, these locations are the attachment sites for the strong forearm muscles, requiring the surgeon to detach or release the muscles from bone in order to apply the plate; this can result in tendinitis and loss of muscle strength. It is difficult for these detached tendon groups to heal back to the bone since there is a bulky plate applied to the normal site of attachment. Moreover, the extensive dissection often strips the bone fragment of its only blood supply, resulting in delayed union, non-union, or even bone death (osteonecrosis).

One approach to treating humerus shaft fractures HF is to use an intramedullary nail 40, as shown in FIGS. 11a and 11b. Intramedullary nails 40 can be effective for treatment of shaft fractures of the long bones and are placed through the central canal of the bone and can additionally be secured on the proximal and/or distal sides with interlocking crossing screws 42, as shown in FIG. 11b. Nails have the advantage of a central position in the canal of the bone, aligned with the neutral axis of the bone and better positioned to resist bending loads. Since they reside inside the bone, nails can be relatively bulky yet avoid the issue of soft tissue irritation. Moreover, since the nail achieves some purchase along the entire inner canal, bending forces are distributed over a wider area of the implant, creating a stronger construct. Nails have an additional advantage over plates since they are not as dependent on thread purchase in bone. Unfortunately, these standard nails are not an effective solution for supracondylar fractures of the humerus, since the canal does not extend into the supracondylar region and the nail would obstruct and interfere with the coronoid/olecranon fossas. There is no rigid nail yet designed that extends along the lateral or medial column distally up into the central canal in the shaft.

Another type of nail that has been used for the treatment of supracondylar fractures of the elbow are the so-called flexible nails 44, such as Enders' nails, as shown in FIG. 12 at the site of a humeral diaphysis fracture HDF. These nails 44 have some degree of flexibility and are passed up through a hole in the medial or lateral epicondyles and directed into the canal proximally. These nails are thin enough to have some flex to them to allow them to curve up past the junction between the central canal in the midshaft of the bone and then flare into the medial or lateral epicondyle. However, because these nails 44 are thin enough to be flexible, they do not provide any effective means for rigid fixation proximally, resulting in motion. In addition, these nails 44 do not provide a means for distal fixation of articular fragments. Finally, because there is a limit to the amount of flexibility in these nails, they have been limited to entry sites at the epicondyles and do not extend fixation down to the condyles where it is often needed. For this reason they have been ineffective for these types of fractures.

A variation of Enders' nails uses a clip that could be attached to the distal end of the nail at the entry site and screwed into the adjacent bone. Although this clip and screw help prevent the nail from backing out and rotating, they do not provide resistance to bending moments or fixation of articular fragments.

Finally, another method of treating supracondylar fractures is to use an external fixator as seen at 46 in FIG. 13, either alone or in combination with other methods. External fixation may not completely or adequately reduce the fracture, and often results in prolonged immobilization and significant residual stiffness and dysfunction. Its use is primarily limited to salvage of very difficult cases. Some of the external fixation devices use rods outside the body on either side of the arm to provide paired attachment sites to crossing pins or wires.

Similar problems and fixation challenges occur with periarticular fractures of long bones at other anatomic locations.

For example, supracondylar fractures of the femur, fractures of the proximal tibial plateau, and pilon fractures of the lower tibia are other sites subject to similar issues caused by large cantilever bending loads, small periarticular fragments size, poor bone quality, and intimate proximity of adjacent vital soft tissue structures at risk with bulky hardware. These other anatomic locations often present nearly identical problems related to existing methods of fixation.

Implants exist that have a portion extended into an intramedullary canal/cavity on a bone with a fracture. One exemplary construction is shown in U.S. Pat. No. 6,706,046. U.S. Pat. No. 6,706,046 discloses an implant with an intramedullary portion that transitions to an offset extension that is secured to a bone part that is produced by a fracture. In this design, the extension is offset from the long axis of the nail toward the side of entry of screws that penetrate the extension, thereby positioning the extension more superficial than the superficial surface of the nail. This configuration allows a nail to be inserted into a tubular bone while facilitating apposition outside the surface of said tubular bone. As depicted in FIG. 14 of U.S. Pat. No. 6,706,046, the implant must initially be placed at a relatively large angle to allow introduction into the intramedullary cavity/canal. As the implant is advanced into the cavity/canal, it is progressively angularly reoriented to allow the offset extension to seat at the unstable bone fragment for connection thereto. Based upon the depicted geometry, the implant would have to be sufficiently flexible to allow placement in its operative position through the above-mentioned assembly routine. The ability to reconfigure the implant lessens its rigidity and thus its ability to stably maintain a relationship between stable and unstable bone parts that are set, utilizing the implant, preparatory to the healing process. In addition, since the geometry of this design is intended to position the extension out through the side of a tubular bone for fixation along the surface of the tubular bone, it cannot be used for fixation of a terminal fragment that extends beyond the tubular portion of the bone, whether said fragment is either inline with or deep to the longitudinal axis of the intramedullary axis of the tubular, bone.

Further, the configuration of the implant makes it impractical for use at many fracture sites.

Implant designers continue to be challenged to make implants with ever greater strength and stability within the geometrical confines of the human body. This is particularly a challenge with implants that reside partially, or fully, within an intramedullary cavity/canal when operatively positioned.

Typically, the intramedullary portion of the implant has strategically located openings to accept fixation components/elements. Jigs/guides are commonly utilized to produce bores in the bone to axially coincide with implant openings that reside within the intramedullary cavity/canal with the implant operatively positioned.

The structural integrity of implants of this type is dictated by the rigidity of the implant itself, the rigidity of the fixation components/elements, and tenacity of the engagement of the fixation components/elements with bone. It is not possible to individually focus on any of these design criteria in attempting performance optimization since these criteria compete with each other.

For example, effective anchoring of the fixation components/elements to the bone generally demands a relatively large diameter, threaded construction to minimize the likelihood of releasing of the fixation components/elements from the bone or bending of the fixation components/elements. Each fixation component/element demands the same diameter opening in the intramedullary portion of the implant. These implant openings potentially weaken the intramedullary portion of the implant.

Designers are thus left with the options of either contending with a weakened implant or increasing the dimensions of the intramedullary portion of the implant to accommodate more robust fixation components/elements. The former option has potentially dangerous consequences. The latter option may produce a construction that is impractical or difficult to use.

The medical profession has generally contended with, and continues to contend with, these problems since no viable solution has been developed to date.

SUMMARY OF THE INVENTION

In one form, the invention is directed to a system for treating a fracture of a bone that produces first and second bone parts separated by a fracture line. The system includes: a first implant having a first body to be placed in an operative position against the bone at one location; a second implant having a second body to be placed in an operative position against the bone at another location spaced from the one location; and a first elongate component that can be directed through the bone to cooperate with each of the first and second bodies so that the first and second bodies and first component together act to maintain the first and second bone parts in a desired set relationship. The first component has a lengthwise axis and cooperates with the first body so that the operatively positioned first component is stabilized by the first body in a first plane that is transverse to the lengthwise axis of the first component. The first component cooperates with the second body so that the first component is stabilized by the operatively positioned second body.

In one form, the first component cooperates with the second body so that the first component is stabilized by the second body in a second plane that is transverse to the lengthwise axis of the first component.

In one form, the first component has first and second ends that engage the first and second bodies respectively at first and second locations so that the first and second ends of the first component are substantially fixed against movement relative to each of the first and second bodies in a direction transverse to the lengthwise axis at the first component.

In one form, the system further includes at least a first fixation element for fixing the first body to the bone at the first location and at least a second fixation element for fixing the second body to the bone at the second location.

In one form, the first and second bodies each has a length and first and second ends spaced in a lengthwise direction. With the first and second bodies operatively positioned, the lengths of the first and second bodies are at least nominally aligned.

In one form, one of the first and second bone parts is a stable bone part and the other of the first and second bone parts is an unstable bone part. The first ends of the first and second bodies are configured to be fixed to the stable bone part each by at least one fixation element with the first and second bodies operatively positioned. The lengthwise axis of the first component is at an angle with respect to the lengths of each of the operatively positioned first and second bodies so as to extend through the unstable bone part.

In one form, the first body is configured to conform to an exposed surface of one of a tibial bone and a humerus bone.

In one form, the second body is configured to reside within an intramedullary cavity of one of a tibia bone and a humerus bone.

In one form, the second body has a portion that projects from the intramedullary cavity with the second body operatively positioned.

In one form, the portion of the second body has a shape that conforms to an exposed surface of a humerus at one of a lateral condyle region and a medial epicondyle region on the humerus.

In one form, there are cooperating locking components on the first component and one of the first and second bodies that interact and lock the first component against movement relative to the one of the first and second bodies with the first component in its operative position.

In one form, the cooperating locking components are cooperating threads.

In one form, the cooperating locking components lock the first component relative to the one of the first and second bodies at a selected angular orientation from within a range of angular orientations.

Cooperating locking components may interact between the first component and each of the first and second bodies to lock the first component relative to each of the first and second bodies at selected angular orientations from within a range of angular orientations.

Cooperating locking components may interact between the first component and at least one of the first and second bodies to lock the one of the first and second bodies against axial movement relative to the first component.

Cooperating locking components may interact between the first component and each of the first and second bodies to lock the first and second bodies against axial movement relative to the first component.

In one form, the first component has spaced first and second ends and there are first cooperating locking components on the first end of the first component and first body and second cooperating locking components on the second end of the first component and second body. With the first and second bodies and first component operatively positioned, the first and second cooperating locking components interlock and lock the first and second ends of the first component substantially against movement relative to the first and second bodies.

In one form, the first component has a body with a stepped diameter with smaller and larger diameter lengths.

In one form, the smaller and larger diameter lengths are both threaded to define the first and second locking components on the first component.

In one form, the portion of the second body has a paddle shape.

In one form, the first component has an end that extends into one of the first and second bodies without being locked to the one of the first and second bodies with the first and second bodies and first component operatively positioned.

In one form, the system is provided in combination with a jig that can cooperate with one of the first and second bodies to facilitate formation of a bore for the first component.

In one form, the second body has at least one opening therein. The system is provided in combination with a jig that can cooperate with the second body to facilitate formation of a bore in bone that aligns with the opening in the second body.

In one form, the first and second bodies and first component are configured so that with the first and second bodies and first component operatively positioned the first and second bone parts reside captively between the first and second bodies.

In one form, the first body has a curved body part and a paddle shape on the curved body part.

In one form, the at least first fixation element is in the form of a pin or a screw.

In one form, the at least second fixation element is in the form of a pin or a screw.

In one form, each of the first and second bodies is configured to conform over substantially its entire length to an exposed surface on a bone with the first and second bodies operatively positioned.

In one form, the system further includes a fixation element that extends fully through the second body.

In one form, the fixation element has an unthreaded length that extends through the second body.

In one form, the fixation element has an entry end and a head end. The head end is threaded and the entry end is unthreaded.

In one form, the invention is further directed to a method of treating a fracture of a bone that produces first and second bone parts separated by a fracture line. The method includes the steps of: providing a system as described above; fixing the first body in its operative position against the bone; fixing the second body in its operative position against the bone; and placing the first component in an operative position by directing the first component through the bone and supportingly against each of the first and second bodies.

At least one of the first and second bodies may be fixed in its operation position after the first component is placed in its operative position.

In one form, the first and second bodies are fixed in their operative positions before the first component is placed in its operative position.

In one form, the step of fixing the first body involves using at least a first fixation element to fix the first body to the bone.

At least one of the first and second bodies may be fixed in its operative position after the first component is placed in its operative position.

In one form, the step of fixing the second body involves using at least a second fixation element to fix the second body to the bone.

In one form, the first component has first and second ends and the step of providing a system involves providing a system wherein the first and second bodies each is elongate with a length between spaced first and second ends. The lengths of the operatively positioned first and second bodies are nominally aligned. The first end of the first component cooperates with the first body so that the first end of the first component and operatively fixed first body are substantially fixed against relative movement in a first line that is substantially parallel to the length of the first body.

In one form, the second end of the first component and the second body cooperate so that the second end of the first component and operatively fixed second body are substantially fixed against relative movement in a second line that is substantially parallel to the length of the second body.

In one form, the bone has a length that is at least nominally aligned with the lengths of each of the first and second bodies.

In one form, one of the first and second bone parts is an unstable bone part and the first component extends into the unstable bone part.

In one form, the first component extends into the stable bone part.

The step of fixing the first body in the operative position may involve fixing the first body against an outside surface of the bone.

The step of fixing the second body may involve directing the second body into an intramedullary cavity on the bone.

In one form, the second body has an exposed portion that projects from the intramedullary cavity on the bone and the step of placing a first component in an operative position involves extending the first component between the first body and the exposed portion of the second body.

The bone may be one of a tibial bone and a humerus bone.

BRIEF DESCRIPTION OF THE DRAWINGS

FIG. 12 is a view as in FIG. 11b wherein the fracture is treated using conventional flexible nails;

FIG. 13 is a fragmentary view of a humerus bone with a fracture treated using a conventional external fixator;

FIG. 26 is a view as in FIGS. 24 and 25 wherein a threaded component is extended into an operative position between the implants utilizing the guide pin;

FIG. 27 is a view as in FIG. 26 with the guide pin removed;

FIG. 28 is a schematic depiction of the components, generally as in FIGS. 24-27, and showing a component operatively positioned between the implants and cooperating structure between the component and implants;

FIG. 29 is a view as in FIGS. 24-27 wherein a jig/guide is operatively positioned to facilitate introduction of a drill or guide pin as shown in FIGS. 24 and 25;

FIG. 34 is a view as in FIG. 33 with a fixation bolt fully operatively positioned;

FIG. 35 is a fragmentary, partially schematic representation of a connection between a screw and component that extends between implants and allows different angular relationships to be selected between the component and the implant;

FIGS. 50-52 are different perspective views of another form of intramedullary implant, according to the invention;

FIG. 53 is a flow diagram representation of a system for treating a fracture of a bone utilizing a system as in FIGS. 50-52;

FIG. 54 is a schematic representation of the system for treating a fracture of a bone, as shown in FIGS. 18-22;

FIG. 55 is a fragmentary, partial cross-sectional view of one specific form of system shown in FIG. 54, and including a fixation component secured to an implant within an intramedullary canal;

FIG. 56 is a side elevation view of a modified form of fixation component usable in a system as in FIGS. 54 and 55;

FIG. 57 is a view as in FIG. 56 of a further modified form of fixation component; and FIG. 58 is a flow diagram representation of a method of treating a fracture of a bone utilizing a system as in FIGS. 54 and 55.

DETAILED DESCRIPTION OF THE PREFERRED EMBODIMENT

Figure 1:
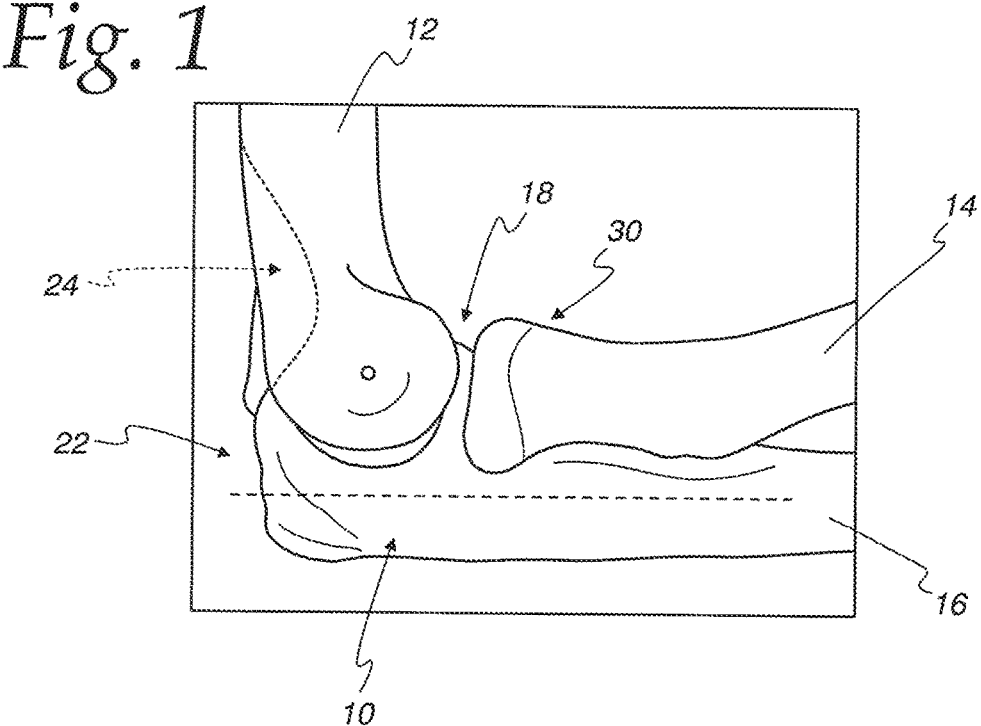
FIG. 1 is a fragmentary, elevation view of a human elbow joint.
Figure 2:
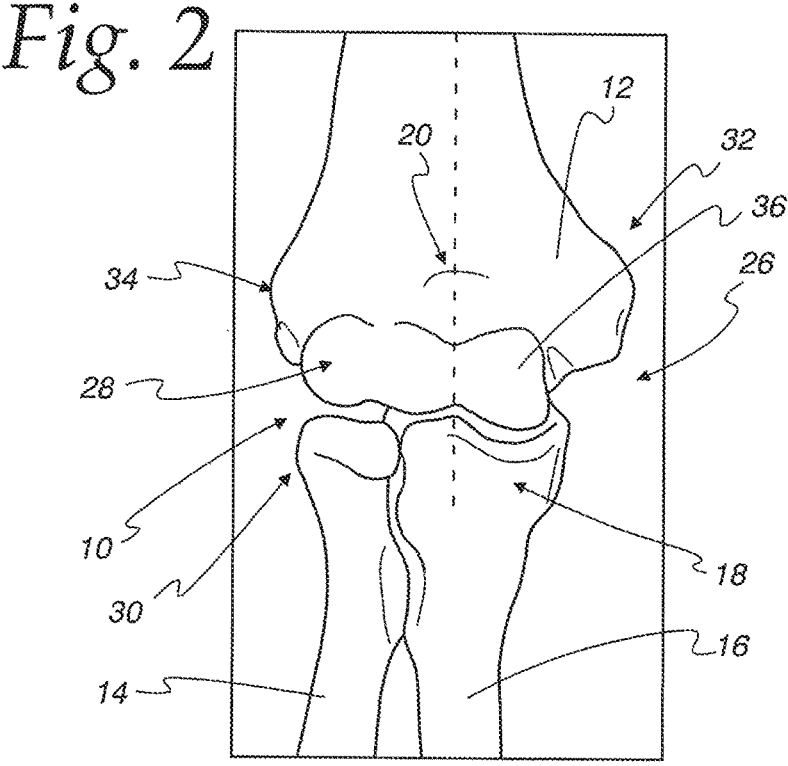
FIG. 2 is a view as in FIG. 1 from a different perspective.
Figure 3:
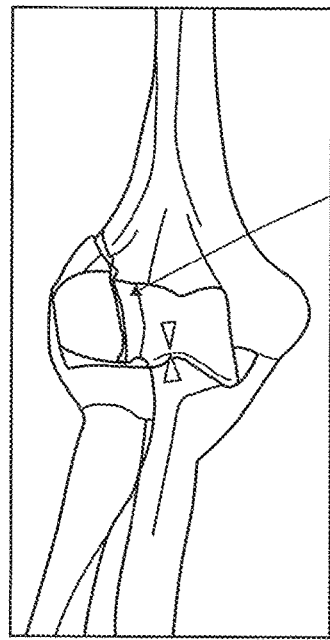
FIGS. 3-8 are fragmentary views of a human elbow joint with different fractures.
Figure 4:
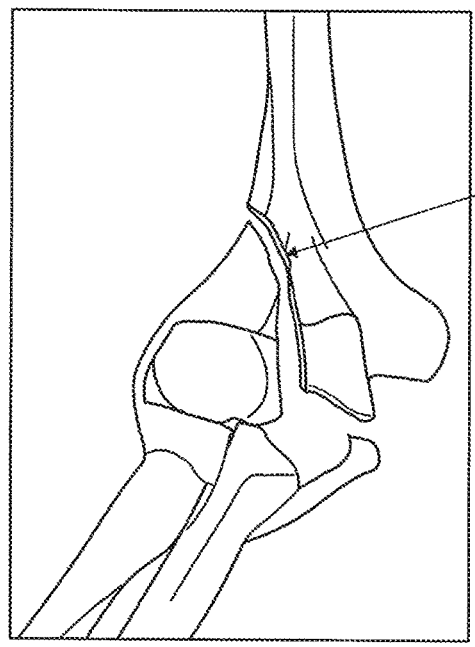
Figure 5:
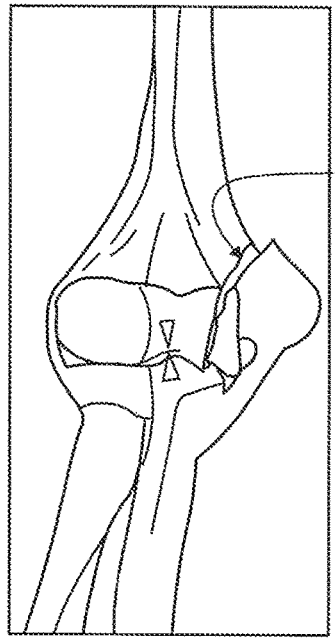
Figure 6:
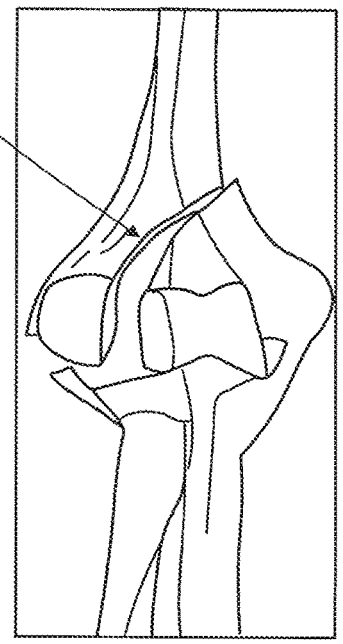
Figure 7:
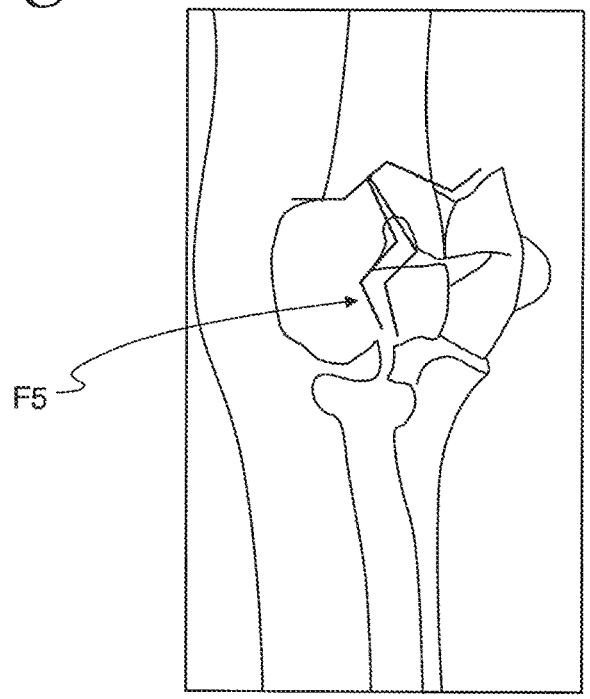
Figure 8:
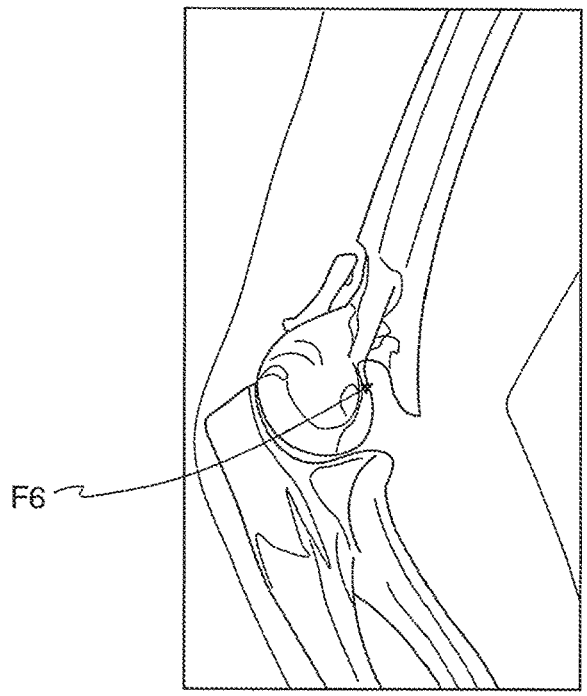
Figure 9A:
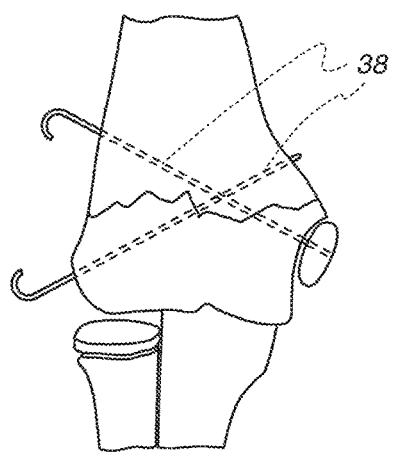
FIGS. 9a-9d are fragmentary views of a human elbow joint with fractures treated using conventional interfragmentary pins.
Figure 9B:
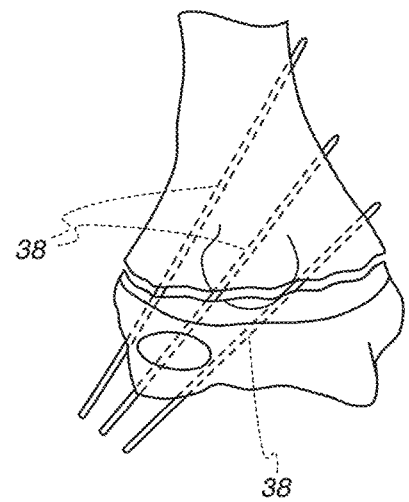
Figure 9C:
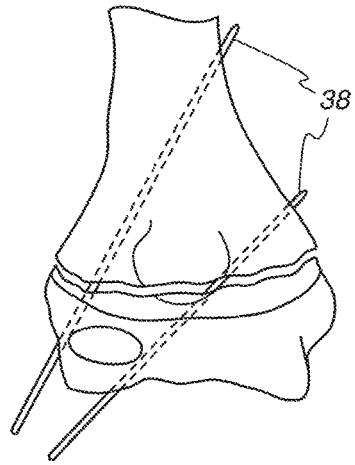
Figure 9D:
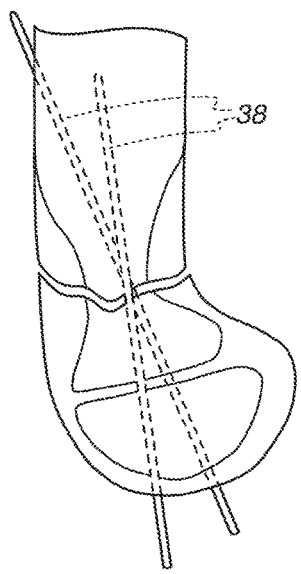

One form of implant, according to the invention and as seen at 100 in FIGS. 14-17, utilizes a plate-like body 110 that, when operatively positioned as depicted, extends along the lateral column 111 of a humerus bone 12 and terminates in a crescent-shaped paddle 112 that fits conformingly against the flat lateral portion of the capitellum 28. The paddle 112 has an enlarged bone contact area that stabilizes the fixation in multiple directions. The plate 110 is fixed with fixation elements such as bone screws 114, either locking or non-locking, through openings 115 along a proximal shaft 116 that has a curvature at least nominally matched to the bone surface it overlies. Distally, the paddle 112 on the body 110 is secured to the capitellum 28 with fixation elements that may be in the form of screws (locking or non-locking) and/or pins (locking or non-locking) 118 as described in U.S. Pat. No. 5,931,839, incorporated herein by reference. One exemplary screw 118 is shown with multiple openings 119 in the paddle 112 for pins. In this way, the implant 100 allows secure fixation of fractures that involve the lateral column 111 with additional fixation of articular fragmentation that involves the capitellum 28. The body 110 extends conformingly along the posterior surface of the distal humerus 12 and then wraps around the lateral epicondyle to terminate in the flat distal paddle 112 that at least nominally matches the shape of, and fits over, the lateral surface of the capitellum 28.

A second form of implant, according to the invention, is shown in FIGS. 18-22 at 120. The second implant 120 is a medial hybrid implant with a body 121 having both a curved intramedullary portion 122 that, when operatively positioned, extends up through the cancellous bone of the medial column and into the medullary canal/cavity of the lower humerus, and an exposed distal portion/end 123 including a flat paddle 124 corresponding to the paddle 112 on the implant 100 that is configured to conform to the humerus 12 at the lateral epicondyle region. The distal end 123 extends out of the lower portion of the medial epicondyle and medial column to terminate at the paddle 124 that sits conformingly against the medial surface of the trochlea to be fixed by fixation elements such as screws and/or pins 126. Pin openings 127 are provided in the paddle 124 with one screw 126 shown therethrough inserted with the assistance of a separable guide pin GP. Proximally, the implant 120 is secured with interlocking fixation elements in the form of screws 128 directed through holes 129.

Figure 21:
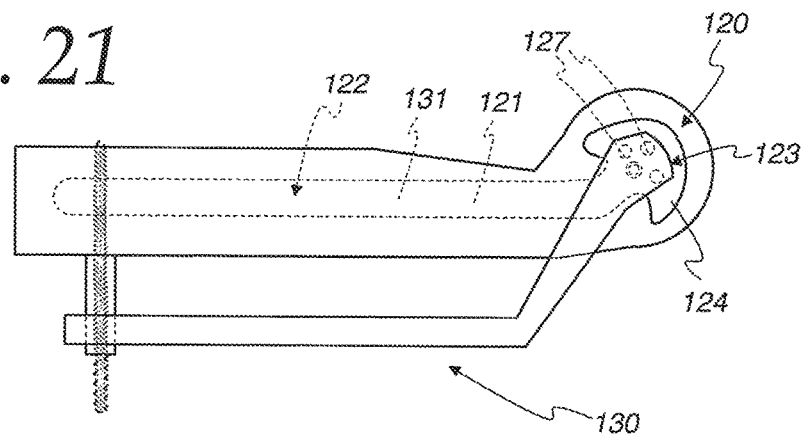
FIG. 21 is an elevation view of the components in FIGS. 18-20, with the bone shown schematically, and with a cooperating jig/guide that facilitates direction of fixation elements into the implant and bone.

As with many other intramedullary devices, a jig/guide 130 is used to drill through the holes 129 for the interlocking screws 128 and attaches at the paddle end of the implant 120, as seen in FIG. 21. Similar jigs/guides can be used for any implant, whether intramedullary or not. The screws 128 may be in the form of set screws that are inserted through one cortex and sandwich a shaft 131, corresponding to the shaft 116 on the body 110, against the opposite cortex, or interlocking screws that may be partially or fully threaded and pass through holes/openings 129 in the proximal intramedullary portion of the implant 120. The latter is preferred.

Figure 22:
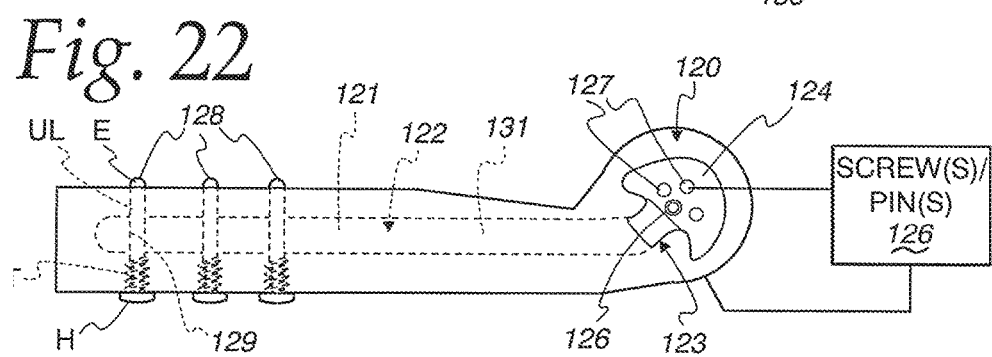
FIG. 22 is a view as in FIG. 21 with fixation elements in place.

In FIG. 22, the screws 128 are shown with bodies each having a head H, threads T at a head end, and an unthreaded length UL between the threads at the head end and the entry end E that is opposite the head end. The entry end E is directed through the bone and into an opening 129 so that the threads T engage the bone and the unthreaded length UL extends into and beyond the body 121.

Figure 20:
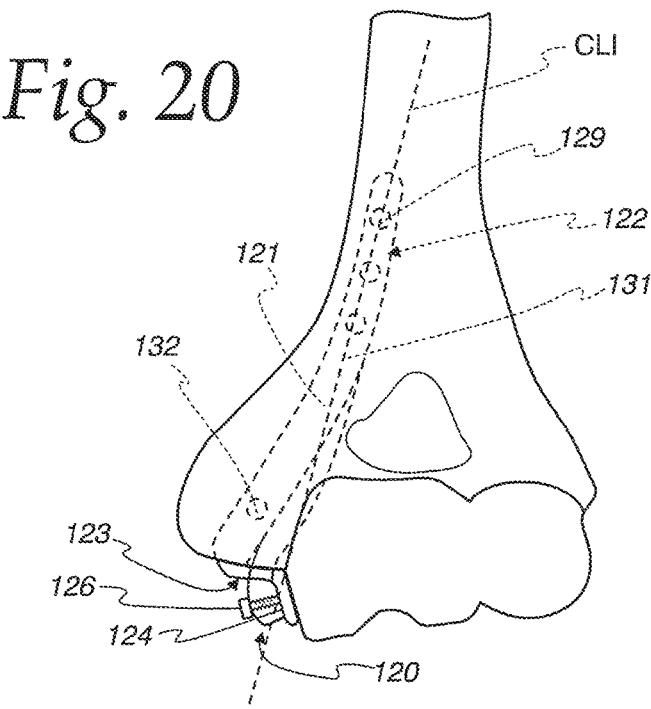

As seen in FIGS. 20 and 21, the guide 130 may be secured utilizing holes formed in the paddle 124 or, more preferably, by forming a referencing hole 132 to support and align the guide 130. The hole may be provided elsewhere but is preferably provided at the location where the referencing hole 132 is shown at the bottom of the rod-like shape of the body within the cavity.

Figure 23:
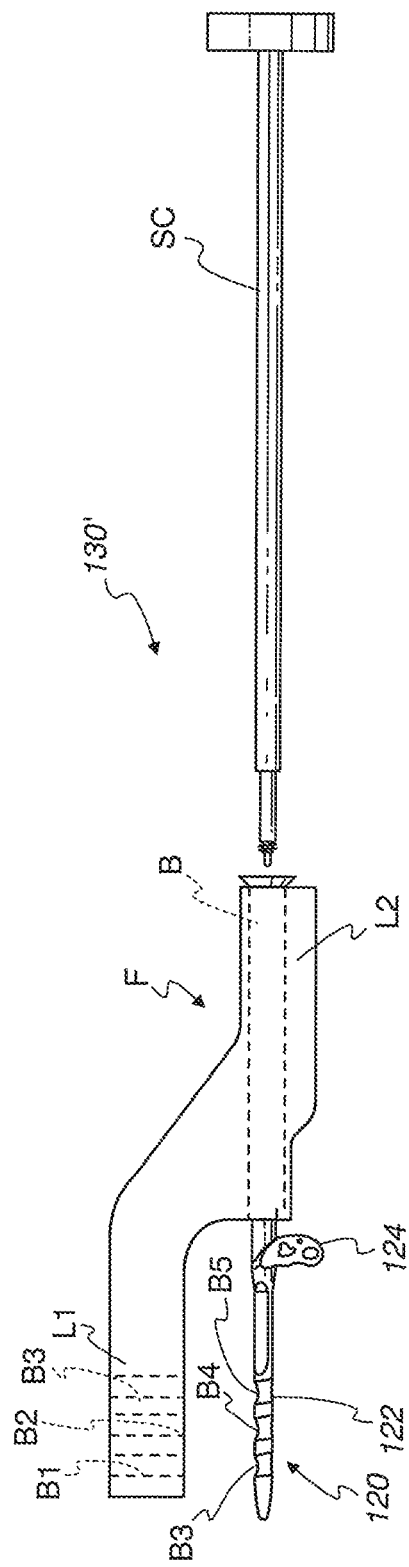
FIG. 23 is an exploded, elevation view of a modified form of jig/guide for the intramedullary implant in FIGS. 18-23.
Figure 24:
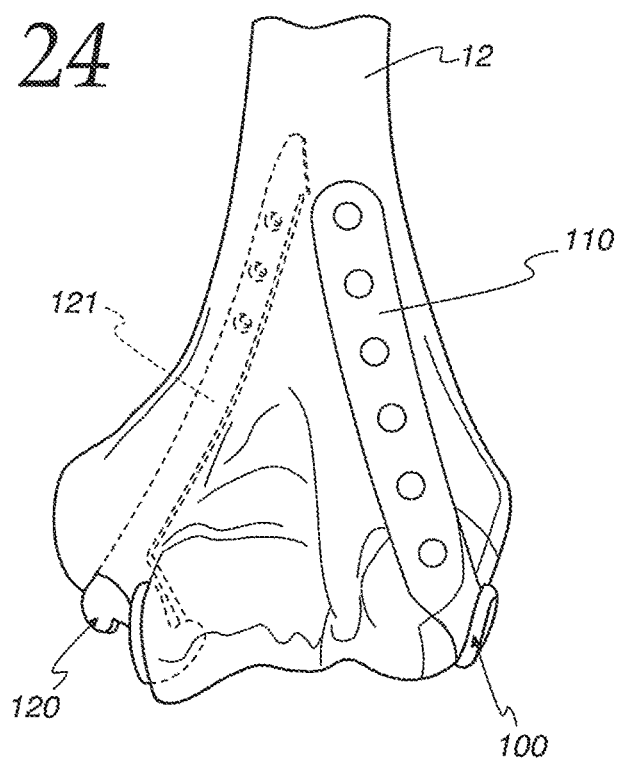
FIG. 24 is a fragmentary view of a fractured humerus with the implants in FIGS. 14-17 and 18-22 both utilized and operatively positioned, according to the invention, on the humerus.

In FIG. 23, a modified form of jig/guide 130' is shown with a frame F that is elongate with offset legs L1, L2, aligned generally with the length of the curved intramedullary portion 122 of the second implant 120. The leg L2 is aligned so that a securing component is guided through a bore B into the implant 120, adjacent to the paddle 124, to allow fixation of the jig/guide 130' to the implant 120. Separate guide bores B1, B2, B3 align with bores B3, B4, B5 successively.

For fractures that involve both condyles of the distal humerus, the two implants 100, 120 can be used together, and form an innovative construct, as seen in FIGS. 23-26.

Generally, the invention contemplates fixing the first and second operatively positioned bodies 110, 121 to the bone 12 at spaced locations by performing at least the step of extending a first component into an operative position between the bodies 110, 121, so that: a) the first component engages each of the bodies 110, 121, so as to be stabilized by the bodies 110, 121; and b) separate stable and unstable bone parts, as shown in FIG. 27 and produced by a fracture line FL. The exemplary condition depicted is an unstable, segmental supracondular fracture wherein there is a stable bone part BP1 and separate unstable bone parts BP2, BP3. The bone parts BP1, BP2, BP3 are maintained in a desired set relationship with each other across the fracture line FL between the bodies 110, 121. The bodies 110, 121 have an elongate form with lengths PL1, PL2, respectively between ends E1, E2 and E3, E4 that are at least nominally aligned with each other and a lengthwise extent of the bone 12, as indicated by the double-headed arrow PL3, with the bodies 110, 121 operatively positioned.

The invention contemplates that there could be more than the two depicted unstable bone parts BP2, BP3 or a single unstable bone part.

Further, the component 144 may extend through only unstable bone parts or through both a stable bone part and one or more unstable bone parts. The component 14 and its counterparts herein inherently function as implant fixation components/elements for their associated implant.

In the simplest form, as shown schematically in FIG. 28, a cross screw/bolt 136 defines the first component and is directed through a hole in the paddle 112, 124 on one implant 100, 120, across a bone 138, which may be the humerus bone, tibial bone, or another bone, and out a hole in the paddle 124, 112 on the opposite implant 120, 100, with each of the implants 100, 120 operatively positioned. It is then secured with a nut 140 to produce a captive arrangement between the nut 140 and a head 142 on the cross screw 136. The screw 136 could be alternatively threaded at both ends to accept a nut at each end. This method may not create a rigid lock to the implants 110, 120, depending upon how the screw 136 interacts with the implant 100, 120, but may, without a locking interaction at the implants 100, 120 eliminate translational movement, angular movement and axial movement of the crossing screw and, when used on the humerus, or other bone, does connect the medial and lateral implants as a structural unit with obvious biomechanical advantages.

Figure 25:
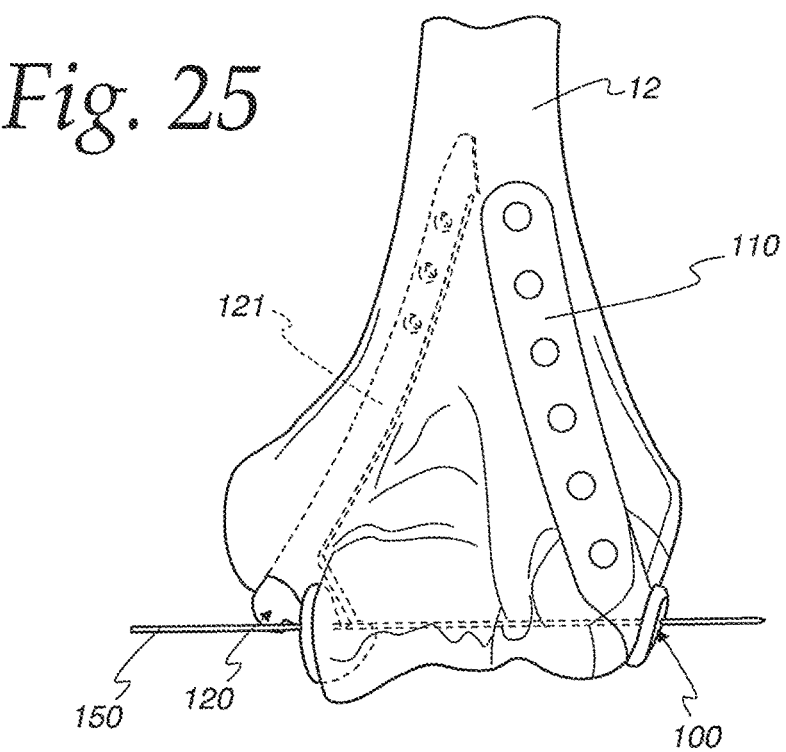
FIG. 25 is a view as in FIG. 24 wherein a guide pin is directed through the separate implants.
Figure 30:
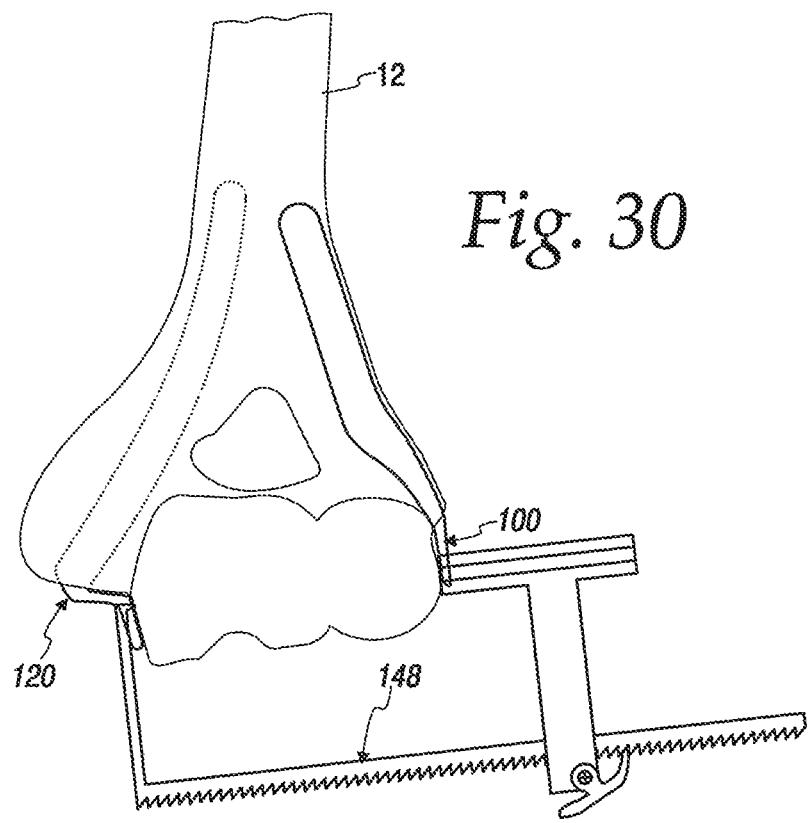
FIG. 30 is a view as in FIG. 29 wherein the jig/guide is reconfigured to engage both implants preparatory to drill or guide pin insertion.

Another method is to pass a first component, in the form of a transcondylar screw 144, as shown in FIGS. 25 and 26, that locks into either one or both of the medial/lateral implants 100, 120. However, since it is nearly impossible to exactly predict the trajectory of this transcondylar screw 144 and the specific location of the paddles on the condyles, it is anticipated that if the holes in the paddles were simply threaded, it would be nearly impossible to match the trajectory of a locking transcondylar screw with the axis of the threads in the plate. There are a number of ways to address this issue, however. One method is to design the implants and the transcondylar crossing screw with different materials so that the threads on the transcondylar crossing screw cut a matching thread in the corresponding hole in the implant. Although this technique has been used to lock the head of a screw within a hole in a surface plate so that it is fixed against any movement within the hole, it has never been used to create a threaded lock of the tip of a screw on implants applied to the opposite side, much less threaded lock on both sides of the crossing screw. Other methods include using an expandable bearing, using a scalloped hole, cross threading, or using a medical grade plastic insert. Locking a crossing screw to only one implant either at the head of the screw or at the tip on an implant on the opposite side of the bone, or locking a crossing screw both at the tip and under the screw head with opposing implants, are preferred, as described below. It has the benefit of markedly reducing loads on both the crossing screw and the implants, allowing the benefit of significantly smaller implants with a construct that has better strength. Locking of the crossing screw at both ends is also contemplated.

While the precise order and manner of assembling the system components are not critical and limited, in one preferred form, one of the implants, such as the implant 120, may be proximally fixed with the other implant 110 loosely and temporarily held, as by pins and/or clamps, preparatory to drilling for the first component/transcondylar screw 144. After drilling and inserting the component/transcondylar screw 144, the implant 110 may be fixed permanently at the proximal location. By performing this sequence, if there is a slight misalignment of the drill relative to the implant 110, the deviation can be compensated for by a slight shifting of the implant 110, on the order of 1 mm, to effect alignment. This sequence can be used for all paired implants utilized. However, as noted above, this sequence is not required as, alternatively, the implants might both be fixed before drilling is carried out to accommodate the first component.

Regardless of the precise mechanism utilized, it is desirable that the ends of the first component be stabilized by the respective body. In one form, this stabilization occurs at one or both of the bodies 110, 121 in a plane transverse to the lengthwise axis of the first component. This stabilization may involve engagement/interaction that blocks relative movement in one or all directions within these planes. In the former case, the ends of the first component may be fixed against movement in one direction (or opposite directions) along a line parallel to the length of the bodies 110, 121. This will avoid unwanted shifting of an unstable bone part, through which the first component extends, relative to a stable bone part to which one or both of the bodies 110, 121 is fixed. Alternatively the ends of the first component may be rigidly fixed to the bodies 110, 121 so that no relative movement can occur.

Figure 31:
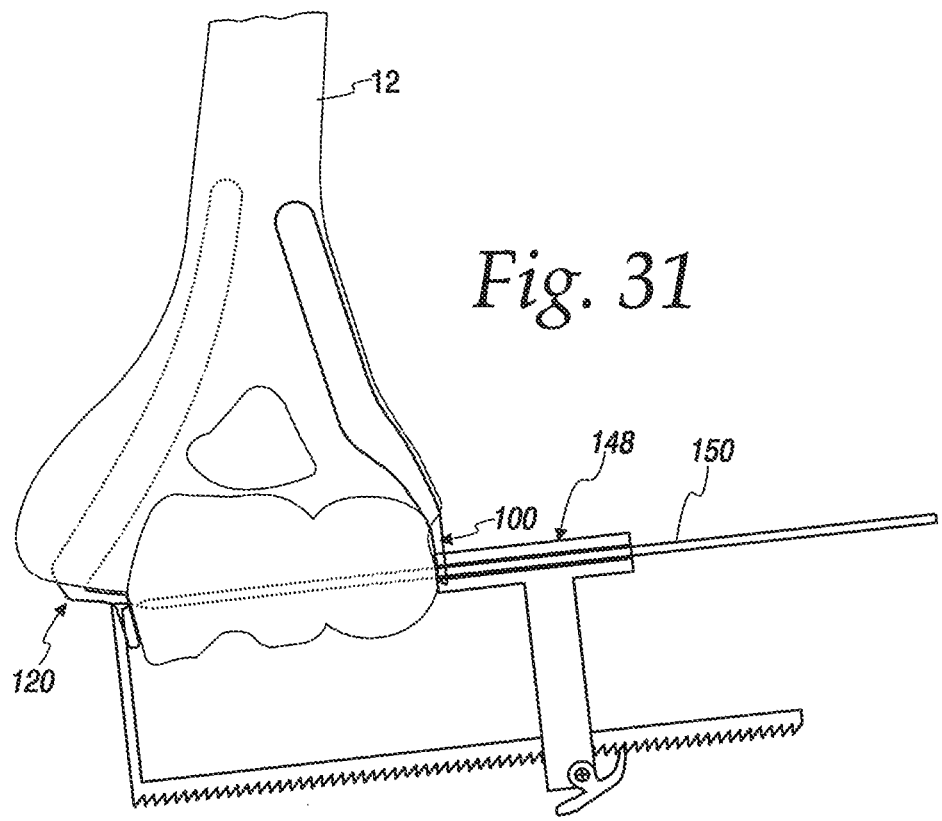
FIG. 31 is a view as in FIG. 30 with a guide pin partially inserted.
Figure 32:
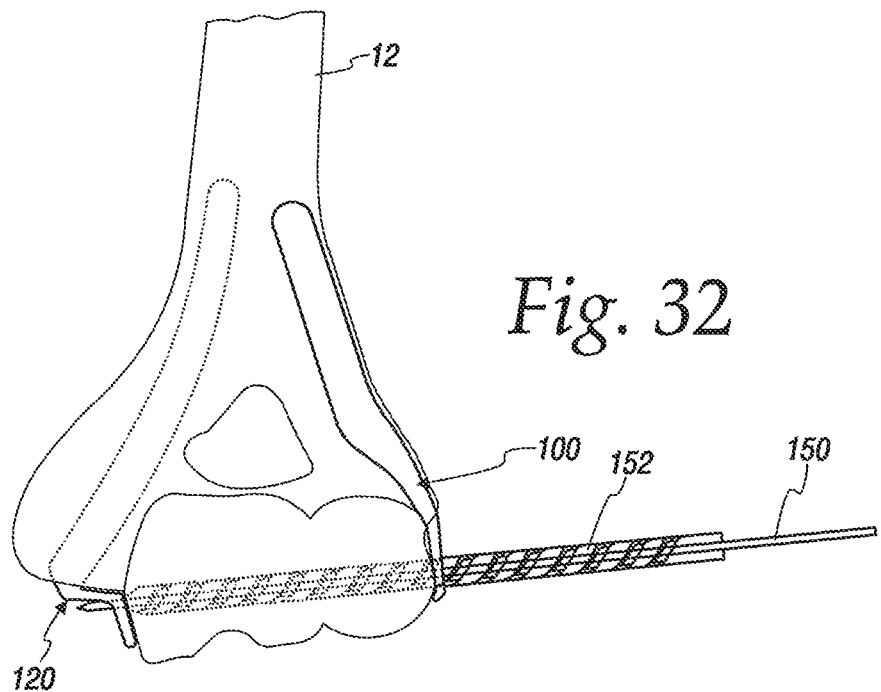
FIG. 32 is a view as in FIG. 31 wherein a drill is advanced over the inserted guide pin to form a bore through the bone between the implants.

One preferred method is disclosed in FIGS. 28-33, and is as used to insert the transcondylar screw 144 with the implants 100, 120 shown in FIGS. 23-26. A hole is formed in the paddle 120 with the assistance of a jig/guide 148. A medical grade plastic insert (PEEK, poly-ether-ether-ketone, or the like) is placed in the hole. Alternatively, injection molded or welded PEEK can be directed into the hole. This plastic would have a small central hole (typically about 0.035"-0.150") that allows passage of a guide pin 150 through its center, as seen in FIG. 31 and also in FIGS. 25 and 26. Once the guide pin 150 is passed across the bone, a cannulated drill 152 is passed over the guide pin 150, as seen in FIG. 32. This drill 152 not only drills a track across the condyles, but also is used to drill an appropriate sized hole through the PEEK insert along the particular trajectory needed for the locking threads of a transcondylar screw 154 that defines the aforementioned first component.

It is also possible to effect drilling without using the guide pin 150.

Alternatively, a locking nut 156/bolt 158 combination is possible, as seen in FIG. 34, with the bolt 158 defining the aforementioned first component and having a head 159. A captive arrangement results between the nut 156 and head 159.

Figure 33:
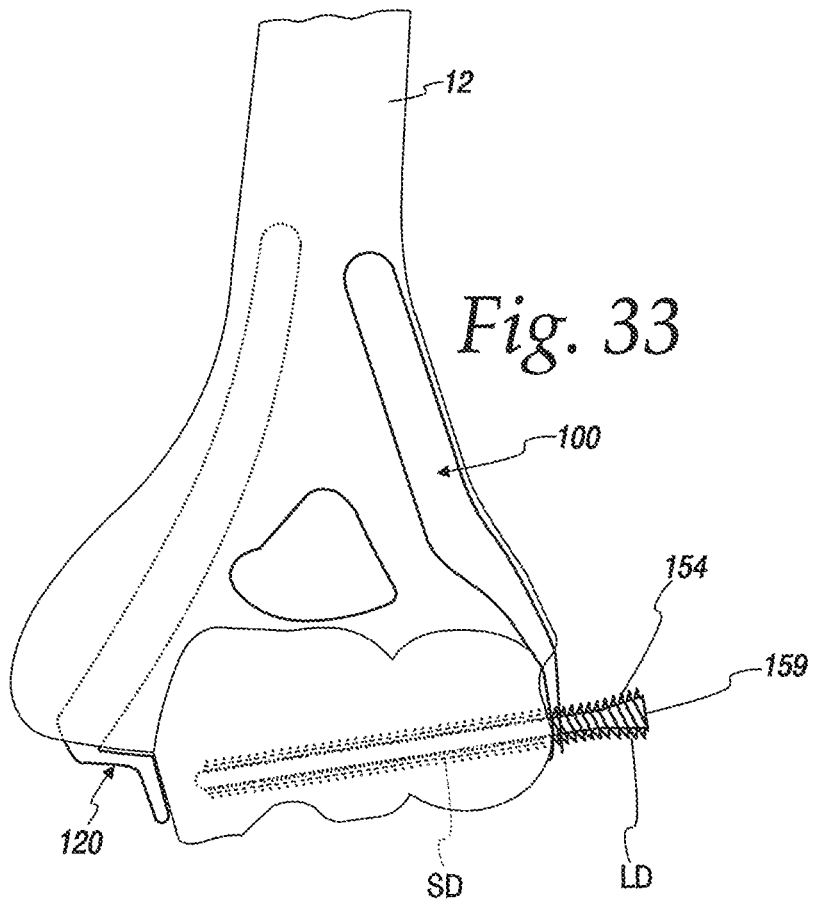
FIG. 33 is a view as in FIG. 32 wherein the drill and guide pin are removed and a fixation screw is advanced through one implant and partially into the bone.

Locking screws, such as the screw 154 shown in FIGS. 33 and 34, are screws that have a thread at the screw head 159 that screws into a threaded hole on a cooperating implant. The depicted screw 154, as the screw 144, has a non-uniform diameter with smaller and larger diameter lengths SD, LD, respectively. The smaller diameter progressively blends into the larger diameter. This design, which may alternatively be stepped sharply at an intermediate location between the smaller and larger diameter lengths, has been available in orthopedics and provides the advantage of eliminating angular motion between the screw and cooperating plate. Because it reduces the need for the screw to rigidly compress the bone to the undersurface of the plate in order to get stability, it creates a stronger construct that is more resistant to pull-out and can be used in situations in which thread purchase is poor (such as osteoporosis). Original locking screws were placed perpendicular to the surface of a cooperating plate and required a drill guide that screws into the hole in order to align the trajectory of the drill with the threads in the plate so that the screw would not bind or cross thread during insertion.

Alternatively, a uniform diameter screw could be used with a taper only at one end, or both ends, thereof.

Polyaxial locking screws allow a screw to be directed in a variety of angles and then form an angularly stable lock to the plate when the screw is fully seated. One of the early methods of forming a polyaxial angular locking screw is disclosed in U.S. Pat. No. 7,195,633, which uses an expandable bearing within the plate to lock as the screw is seated. The disclosure in this patent is incorporated herein by reference. Other designs have used dissimilar metals in which the screw metal is harder than the plate metal and cuts a screw track in the hole as it is seated. Another design uses a triangularly-shaped, or other polygonally shaped, head that creates a lock in a hole with a complementary triangular, or other polygonally shaped recess, in it. Another design utilizes a threaded screw in a threaded hole with threads only present partially around the circumference of the hole or the circumference of the screw.

In another form, as show in FIG. 35, a locking hole LH is shown in a paddle P that is part of an implant. The locking hole LH has cutouts CO that interrupt threads over approximately 50% of the circumference of the locking hole LH. A cooperating screw 15 can then cross thread at different angles. Partial threads could be present alternatively on the screw or both on the screw and around the locking hole LH. Potentially, this connection will lock the screw against both translational and angular movement within the locking hole LH. The screw becomes effectively fixed in a specific orientation and depth within the locking hole LH. Different angular and depth locations can be selected.

In addition, locking of the leading tip of the screw can be achieved by selecting the appropriate design parameters that include hole diameter, number of thread leads, top and bottom surface chamfer, material properties of the implant and screw, percentage of engaged thread circumference, and leading and trailing screw diameters.

Yet another design uses an insert of PEEK that is either pressed into or welded around the hole or injection molded into the hole. Like the dissimilar metals, the threads of the screw cut a threaded track into the PEEK to lock it in place. The screw head can be conical to expand in the PEEK as it is screwed home.

To date, all locking screw designs are limited to screws that are placed into a single plate. They all lock with threads at the screw head. Because locking screws have this limitation, they are ail loaded in cantilever bending, with the result that the screws need to have a relatively large diameter to handle the applied load. There are situations in which this relatively large size is detrimental.

Figure 36:
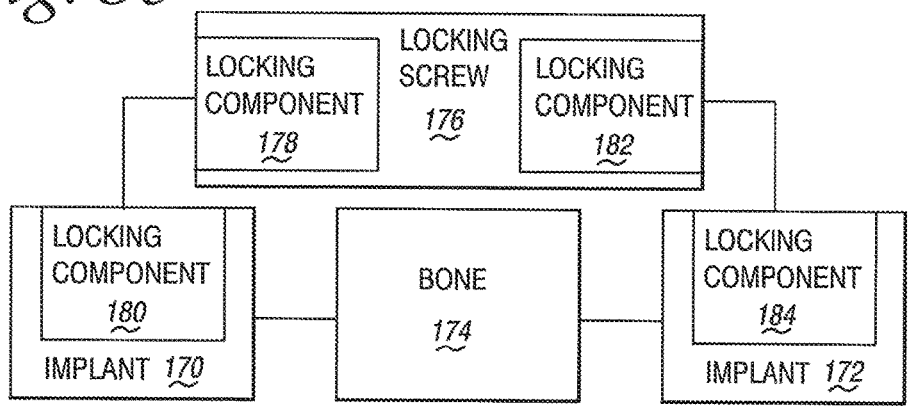
FIG. 36 is a schematic representation of components of the type in FIG. 34.

In one form of the invention, as shown schematically in FIG. 36, a pair of implants 170, 172 is provided with the implants 170, 172 having bodies partially or entirely in spaced relationship, as on opposite sides of a bone 174 that may be any bone such as, but not limited to, a tibial bone, humeral bone, or other bone at which there is a fracture. A component, as in the form of a locking screw 176, is locked simultaneously through: a) cooperating components 178, 180, respectively on the locking screw 176 and implant 170 at one location; and b) cooperating components 182, 184, respectively on the locking screw 176 and implant 172 at a second location that is spaced from the first location. The components 178, 180, 182, 184 are preferably, but not necessarily, cooperating threads. The locking screw may have a head and tip at which the threads 178, 182 are formed. The locking screw 176 may have other configurations.

Alternatively, the locking screw might lock to either one, but not the other, of the implants 170, 172. The locking screw might, with this variation, be supported in non-locking relationship by the other of the implants 170, 172.

Figure 10:
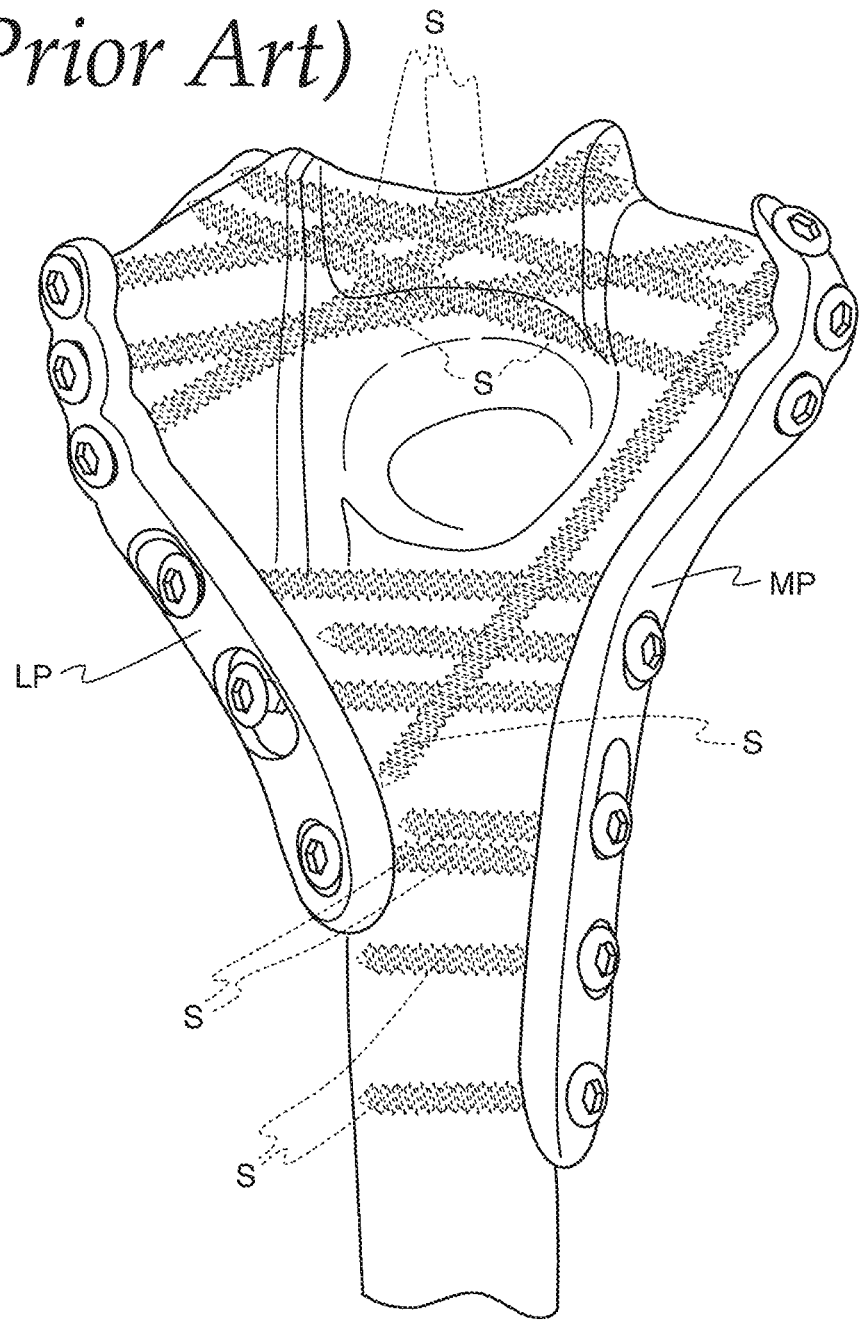
FIG. 10 is a fragmentary view of a fractured humerus treated with conventional implants/plates that are fixed with screws to separate bone parts separated by a fracture line.

The generic depiction of implants 170, 172 is intended to encompass any arrangement, of separate, cooperating implant components, including intramedullary implants in medial/lateral columns, plates along medial/lateral columns, etc., including different combinations thereof. For example, both implants 170, 172 may be elongate plate-like structures configured to conform over substantially their entire length to exposed surfaces on a bone that reside therebetween as in the prior art system of FIG. 10.

It is believed that this concept has not been derived from existing technology by those skilled in this field because of at least the following. If the holes are pre-formed as with the original locking screw technology, it would require that a hole is drilled first along a trajectory that allows both plates to be applied with both holes aligned exactly at the same trajectory, in order to allow the threads of the crossing screw to engage both sides. This is too difficult to be surgically practical.

Figure 37:
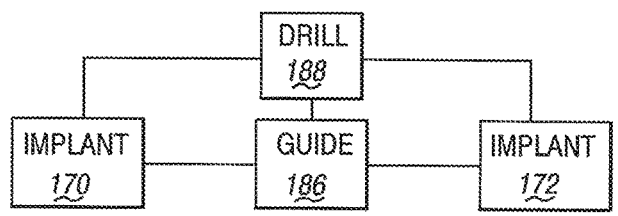
FIG. 37 is a schematic depiction of a drill guide for facilitating insertion of a component as in FIG. 34.

However, by combining and modifying polyaxial locking technology as described herein, this problem can be overcome. A jig/guide is used, as shown schematically at 186 in FIG. 37, for a drill 188 to form the aligned holes in the implants 170, 172, and requires that the angle of trajectory falls within the polyaxial locking range that is possible (currently a max of 30-35 degrees).

With the supracondylar implant, a PEEK insert might be utilized. Since it may not be known if the angle of insertion will fall outside of the 30 degree range, the appropriate drill hole can be formed through the PEEK during a surgery using a guide pin 150 placed first as described above relative to FIG. 32.

The invention can be practiced and adapted, based upon the principles herein, to address one or more of at least the following objectives.

1. The design may improve the stability of fixation by triangulating the fixation along the medial bone column, along the lateral bone column, and coupling these two columnar fixation implants with a horizontal fixation element that connects the two. Since the horizontal crossing screw distally is captured on both sides by the columnar implants, the two point fixation eliminates the cantilever bending on the crossing screw. In turn, this allows the crossing screw to be much smaller in diameter, decreasing the risk of iatrogenic comminution of a distal fragment with a large screw hole and reducing the risk of soft tissue irritation from the head of the screw.

Connecting the medial and lateral column implants with a captured crossing screw also distributes the bending load over a wider composite structure, thereby reducing the implant loads and allowing thinner implants to be used. It is also better at maintaining length of the bone, even in situations in which there may be segmental fracture elements between the shaft of the bone proximally and the joint surface distally.

Ideally, this horizontal element is locked to both the medial and lateral columnar implants, but it is still an improvement if it is locked on only one side, or even unlocked at both sides.

2. The design may reduce soft tissue irritation by using an intramedullary implant that is designed to extend from the shaft down into the central portion of either the medial or lateral column. In one preferred form, this is a hybrid intramedullary implant, being intramedullary in the shaft and medial (or lateral) column and terminating in a superficial plate that provides holes for screw fixation into the peri-articular fragments distally.

3. The design may achieve fixation of supracondylar elbow fractures with fixation on both columns where at least one implant is intramedullary and designed to extend from the shaft down into the medial (or lateral) column. Specifically, this includes: (1) fixation with a medial intramedullary implant and a lateral plate; (2) fixation with a lateral intramedullary implant and medial plate; or (3) fixation in which both columns are fixed with intramedullary implants.

4. The design may avoid stripping of the flexor tendon attachments on the medial epicondyle by eliminating the need for a plate that is applied to the surface of the medial column. If a lateral column intramedullary implant is used, this eliminates stripping of the extensor tendon attachments to the lateral epicondyle.

5. The design may provide a solution for what intuitively seems an impossible design issue—using a solid intramedullary device that also extends and captures the distal end of the humerus. The intramedullary canal of the humerus is a long, straight open canal within the central shaft and terminates just proximal to the coronoid/olecranon fossa. Because of this anatomy, the possibility of using a solid nail that allows intramedullary fixation proximally yet provides fixation of the peri-articular surface seems intuitively impossible. The current invention solves this problem by drilling and/or broaching an intramedullary track up through the porous metaphyseal bone of the medial (or lateral) column and then accurately designing a fixed implant with a specific diameter and curve to compensate for the curvilinear path into the central canal of the humeral shaft. The implant design must allow insertion of the implant through the curved track, yet be large enough to provide interlocking screw holes for stabilization of the implant proximally within the shaft. Accurate placement of the starting hole and broaching of the passage along the column is also important to allow the nail to pass up into the bone.

6. The design may combine the benefits of plate and screw fixation at the distal end of the bone with the benefits of an intramedullary rod fixation in the canal of the long bone (humerus). The distal peri-articular fragments have limited area for purchase; these are best secured with a low profile plate and screws. On the other hand, by combining this distal plate portion or paddle with an intramedullary implant proximally, the implant can be thicker and better suited to resist the large bending moments. In addition, since it is contained within the bone canal, it is better suited mechanically since distribution of bending forces occurs over a large distance within the canal. The intramedullary position also eliminates the problem of soft tissue irritation (since it is within the bone). The position of the paddle predominantly in line to the long axis of the intramedullary canal reduces bending loads on the implant that can occur with prior designs that utilize a significant superficial offset.

This implant design may overcome the problem of stabilizing small articular fragments to the stable proximal shaft which are at a considerable distance from the articular surface. The design may overcome the problem of maintaining position of the distal articular surface in terms of joint anatomy and maintenance of length in the context of segmental fracture components extending up into the medial/lateral columns. The design may overcome the difficulty of fitting a plate to the complex geometry of the medial column of the distal humerus. The design may overcome problems of external bulky hardware interfering with the soft tissues and avoids extensive stripping of critical tendons and other soft tissues. When both implants are locked to each other with a distal transcondylar cross bolt/screw, this design creates an integrated structural unit that extends from the medial to the lateral side, vastly improving the stability of fixation and allowing accelerated rehabilitation and improved recovery of motion.

Figure 11A:
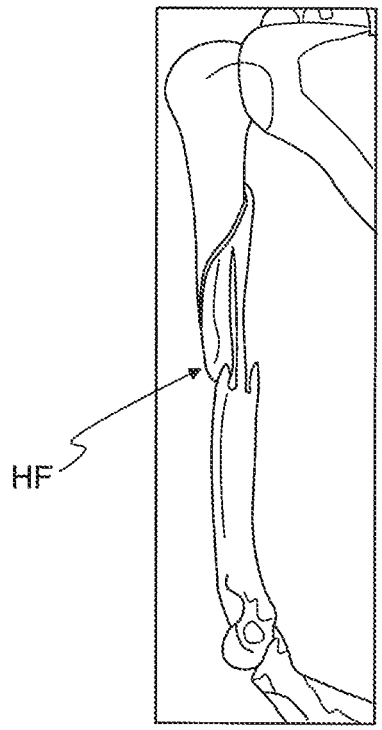
FIG. 11a is a fragmentary view of a humerus bone with a shaft fracture.
Figure 11B:
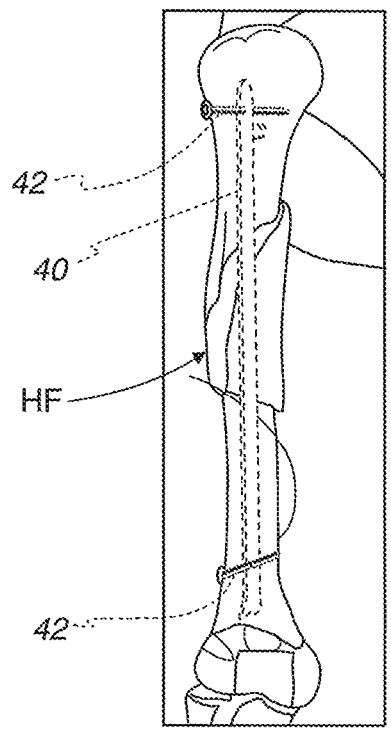
FIG. 11b is a view as in FIG. 11a with the fracture treated utilizing a conventional intramedullary nail secured using screws.
Figure 14:
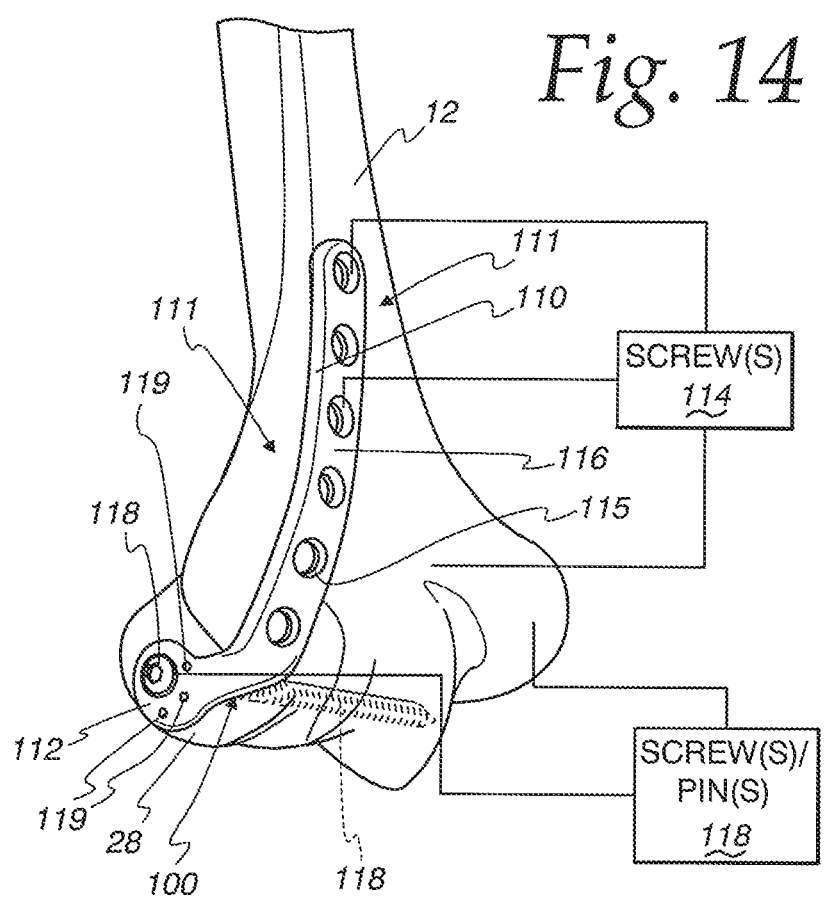
FIGS. 14-17 are fragmentary views of a fractured humerus bone with an implant along the lateral column thereof, according to the invention, with each of the Figures showing the components from different perspectives.
Figure 15:
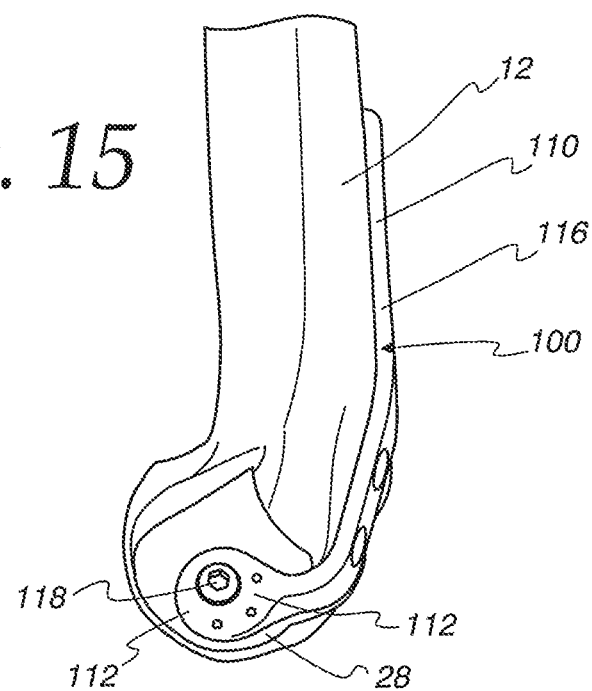
Figure 16:
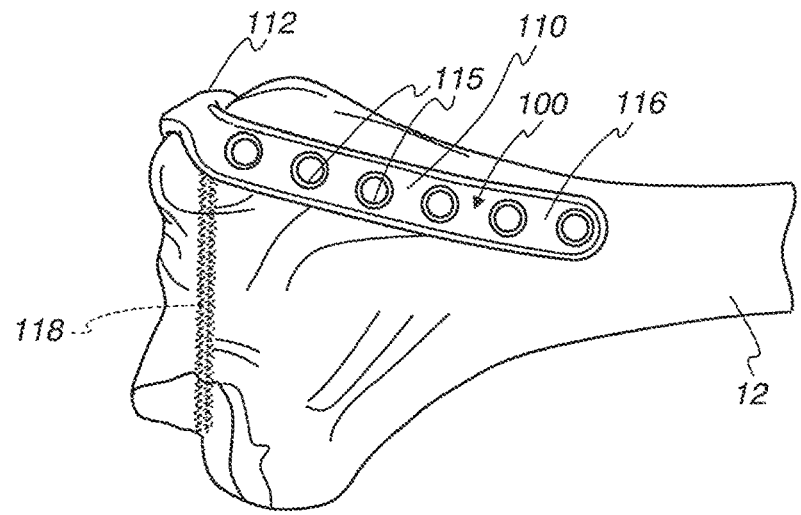
Figure 17:
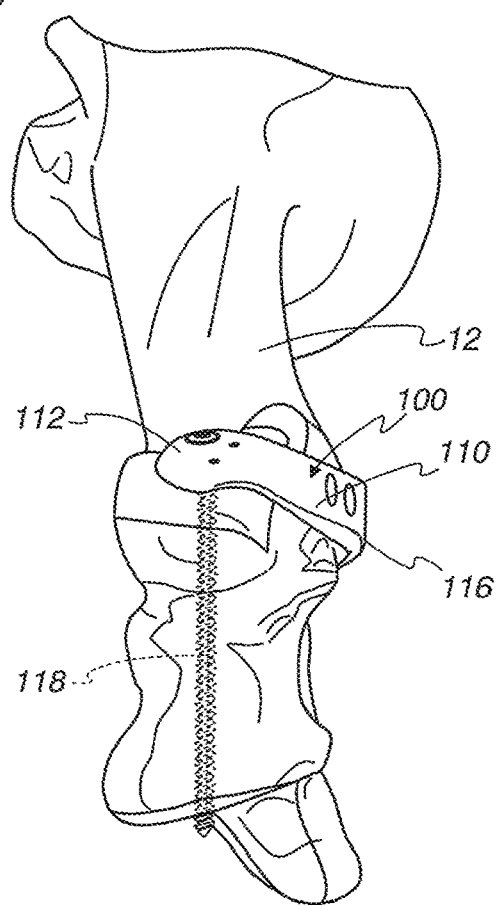
Figure 18:
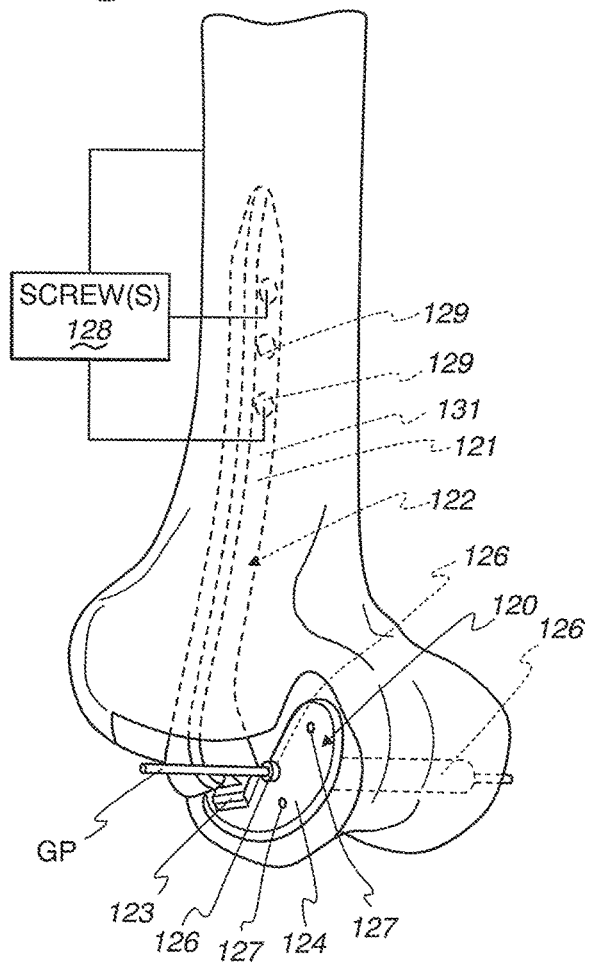
FIGS. 18-20 are fragmentary views of a fractured humerus bone with an implant, according to the invention, within the medullary canal of the lower humerus and with an exposed portion thereof conforming to a medial portion of the humerus and with the components in FIGS. 18-20 seen from different perspectives.
Figure 19:
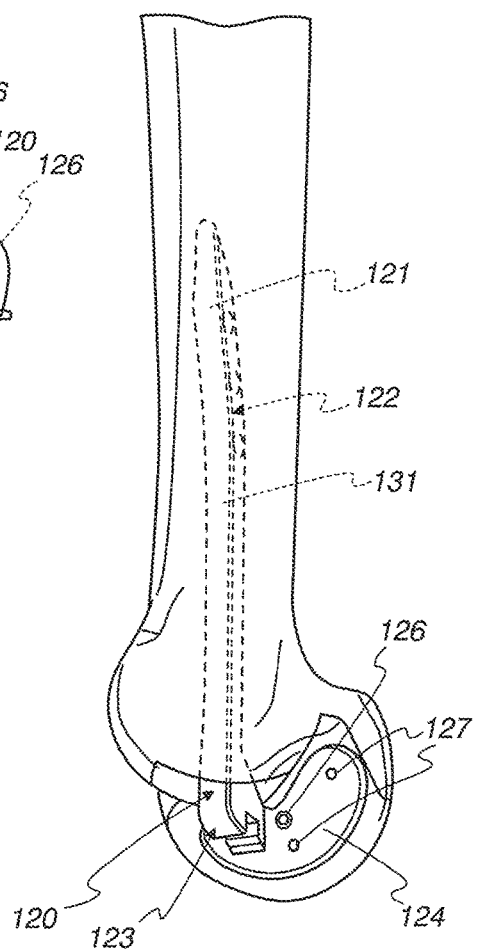

Another aspect of the invention relates to the fixation of intramedullary nails, as seen in FIGS. 11a and 11b and implants such as the implant 120, as described herein.

The problem with interlocking a supracondylar nail in the humerus or other bones with small canal diameter relates to size. Standard interlocking screws are fully threaded (with a self-tapping tip). The hole in the nail needs to be larger than the thread diameter in order to allow the screw to pass. The interlocking screw obtains thread purchase on either side of the bone.

A supracondylar nail would need to be typically only about 5 mm-6 mm in diameter in order to allow it to pass through the medial or lateral column. A standard screw size is a 3.2 mm screw (3.2 mm thread diameter, 2.3 mm core diameter). If a 3.5 mm hole is provided that is wide enough to allow the interlocking screw to pass, there is less than 1 mm 1.3 mm of wall thickness on either side of the nail at the region of the hole. This is likely to cause the nail to break at the screw hole. Although a 2.3 mm screw would improve the wall thickness of the nail, this smaller screw has only a 1.75 mm core diameter and is not strong enough to handle the required loads.

The current invention offers a solution to allow cross fixation of a nail/implant, corresponding to the implant 120, of limited diameter with an interlocking screw that maximizes strength. In its simplest form, the screw is threaded for a length just beneath the screw head to provide thread purchase of the bone cortex immediately under the screw head. This locks the interlocking screw to the bone and prevents the screw from angulating or backing out. The remainder of the screw is smooth with a diameter that is just smaller than the hole in the nail and extends into a nearly press-fit hole through the opposite bone cortex. This provides further stability against angulation of the screw, but allows a larger screw diameter through the nail than if the screw was fully threaded.

Figure 38:
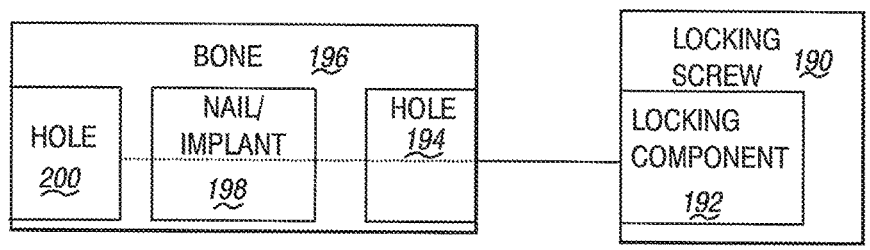
FIG. 38 is a schematic representation of a system as shown in FIG. 22.

As shown schematically in FIG. 38, a 3.2 mm screw 190 can be used with greater strength of fixation resulting. The locking screw 190 has a locking component 192 at one location that may be in the form of threads right below a head of the screw 190. The locking component 192 fixes, as by being threaded, within a hole 194 formed in a bone 196. The remainder of the length of the screw 190 extending beyond the locking component 192 would be a smooth, unthreaded cylinder which passes through a nail/implant 198 and into an aligned hole 200 in the bone 196 on the other side. In this way, the connection affords the strength of the 2.3 mm core diameter passing through the nail/implant 198 and out of the far surface of the bone 196, but retains a threaded purchase of the bone 196 on the near side. All that is lost is the thread purchase of the bone on the far side, but since the threads primarily only keep the screw from backing out, this should not be significant.

Alternatively, the locking screw 190 could lock to the nail/implant 198, as through cooperating threads, or another mechanism.

This is a solution that has particular utility for other small implants that use small interlocking nails. The concept can be practiced at any bone location. One or more locking screws 190 can be utilized and may be directed into the nail/implant 198 from one direction or from opposite directions.

The nails/implants 198 can be made with a flexible configuration. More preferably, the nails/implants 198 have a fixed shape that is either straight or bent. The fixation of the nails/implants 198 is strengthened by the presence of a paddle, such as the aforementioned paddle 124. The enlarged area of the paddle 124 affords a potentially substantial bone contact area that makes possible multi-directional reinforcement of the associated nail plate.

Figure 39:
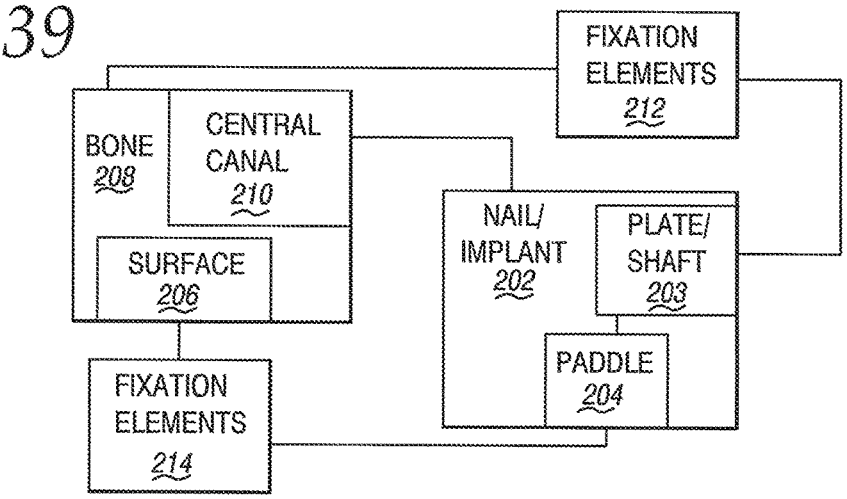
FIG. 39 is a schematic representation of a modified form of system, generally as shown in FIG. 38.

In another form, as shown in FIG. 39, an intramedullary nail/implant 202 corresponding to the implant 120, has a plate/shaft 203 that is contiguous with a flat paddle 204. The flat paddle 204 is contoured to fit along a surface 206 of a bone 208, which bone surface 206 is perpendicular to a convex articular surface (i.e., capitellum or trochlea as opposed to a concave articular surface such as the distal radius), with the nail/implant 202 in a central bone canal 210. Fixation elements (screws, pins, etc) 212 that are distributed through a corresponding arrangement of holes, as described above, fix the plate/shaft 203 relative to the bone 208. Fixation elements 214, as described above, secure the paddle 204 to the bone surface 206.

In FIGS. 40-43, different combinations of implants contemplated by the invention are shown. The implants are not described hereinbelow in any detail but could take the form of any of their counterparts, described above, for external surface application and for at least partial placement within an intramedullary canal/cavity.

Figure 40:
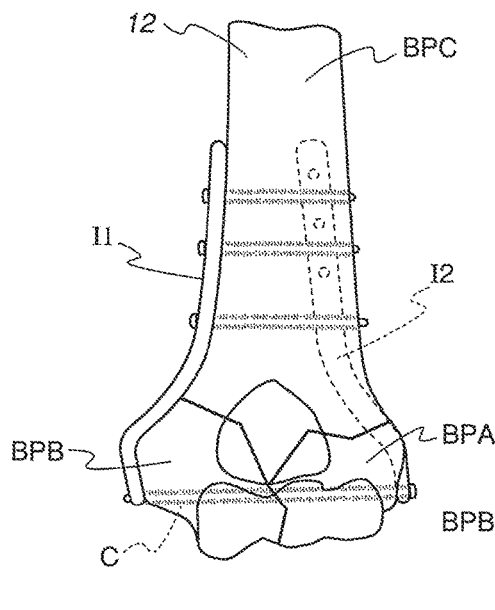
FIGS. 40-43 are fragmentary, elevational views of a fractured distal humerus with different combinations of implants contemplated by the invention.

In FIG. 40, implant I1 is shown as a medial plate with implant I2 as a lateral plate, with both implants on the outer surface of the distal humerus and used to stabilize bone parts BPA, BPB relative to a stable bone part BPC. Both implants I1, I2 are on the external surface of the distal humerus 12. A component C, corresponding to the first components described hereinabove, extends between the implants I1, I2 and interacts therewith utilizing any of the structures described above.

Figure 41:
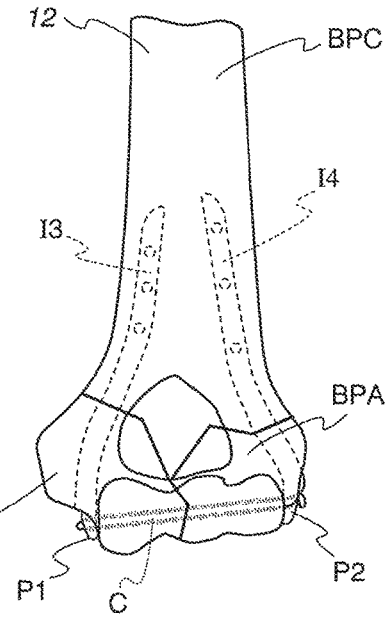

In FIG. 41, implants I3, I4 each resides within the intramedullary cavity on the distal humerus 12 and has a paddle P1, P2 projecting therefrom, respectively at medial and lateral locations. The component C extends between the paddles P1, P2.

Figure 42:
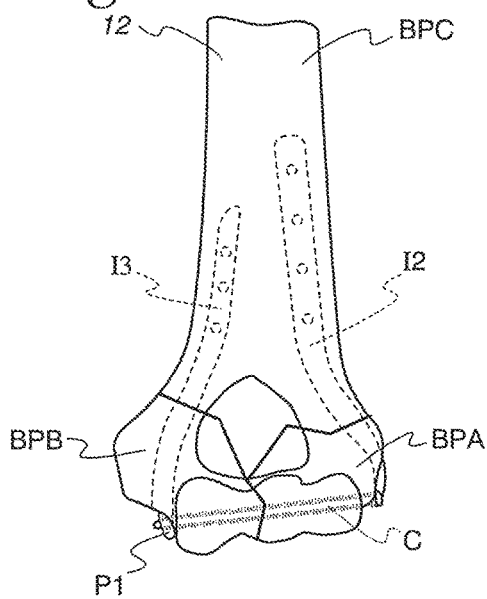

In FIG. 42, the medial column intramedullary implant 13 is used in combination with the lateral plate implant I4. The component C connects between the paddle P1 and the externally located implant I2.

Figure 43:
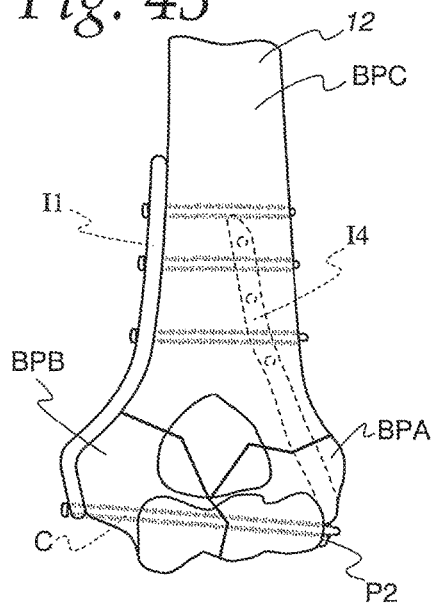

In FIG. 43, the medial plate implant I1 is used in combination with the lateral column intramedullary implant I4. The component C connects between the externally located implant I1 and the paddle P2.

Figure 44:
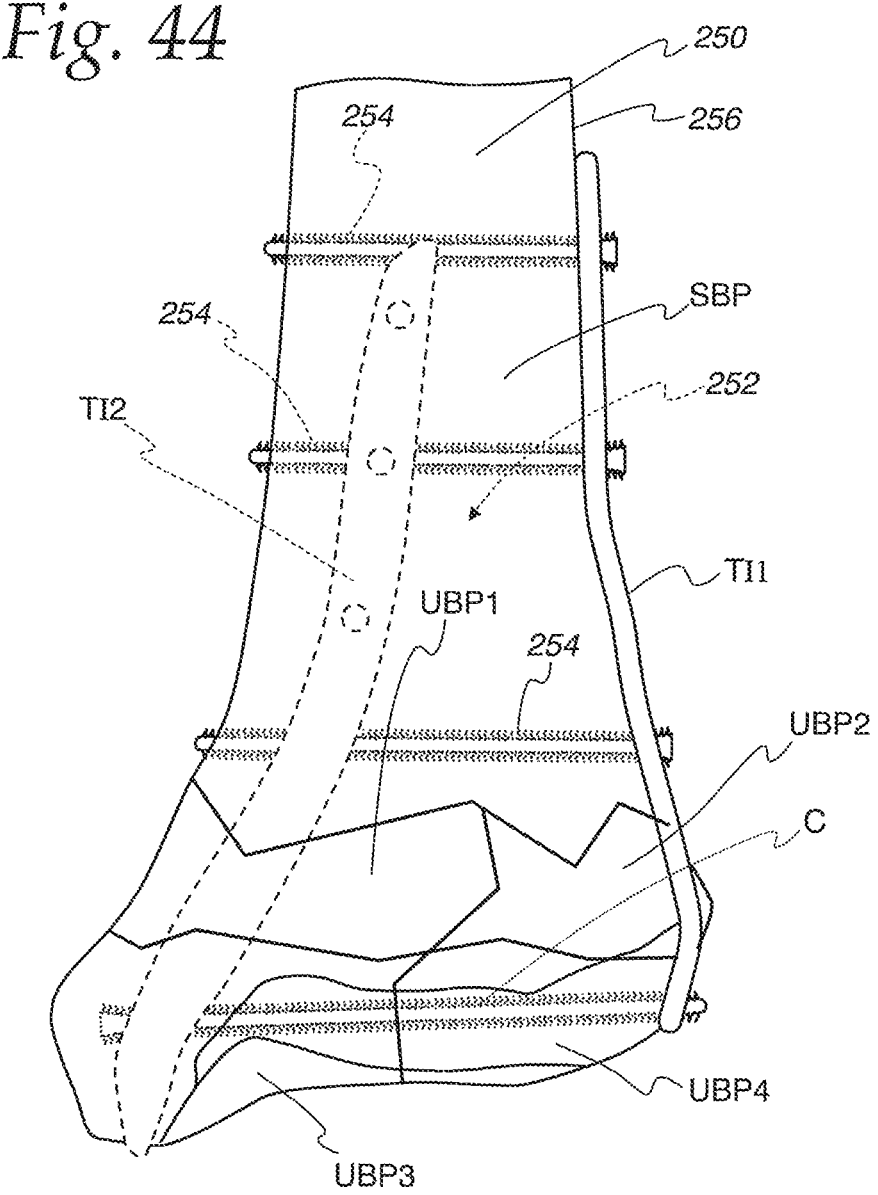
FIG. 44 is a fragmentary, elevational view of a distal tibia region with implants according to the present invention utilized to treat a fracture thereat.
Figure 45:
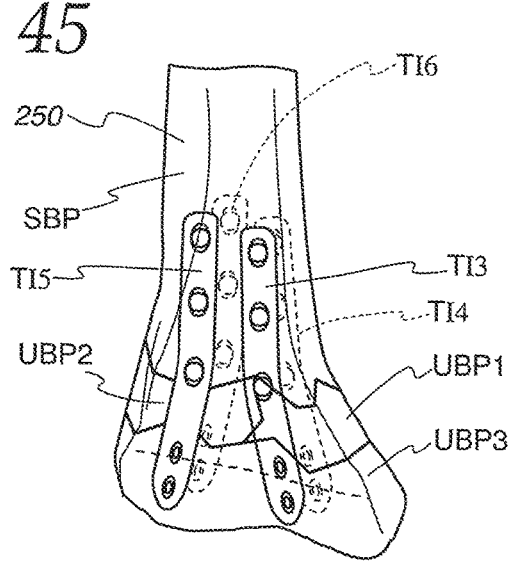
FIG. 45 is a view as in FIG. 44, with the distal tibia turned through 180° and with different arrangements of different implants, according to the present invention.

In FIGS. 44-47, the invention is shown as used to treat a fracture of a tibia 250 that in FIG. 45 produces a stable bone part SBP and unstable bones parts UBP1-UBP4.

Referring initially to FIG. 44, an implant TI1 is located on the outside of the tibia 250, with a separate implant TI2 situated in an intramedullary cavity 252 on the tibia 250. Fixation elements/components 254 secure the implant TI1.

A component C, corresponding to the aforementioned first components, interacts between the implants TI1, TI2, in any one of the various manners described above.

In this embodiment, the component C extends through the unstable bone parts UBP3, UBP4. The implant TI1 is shown at a lateral location with a configuration conforming to the tibial surface 256.

Figure 46:
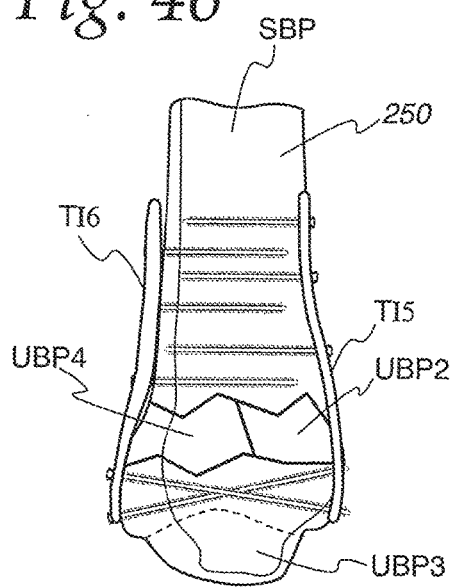
FIG. 46 is a view of the components as in FIG. 45 but taken from the medial side.
Figure 47:
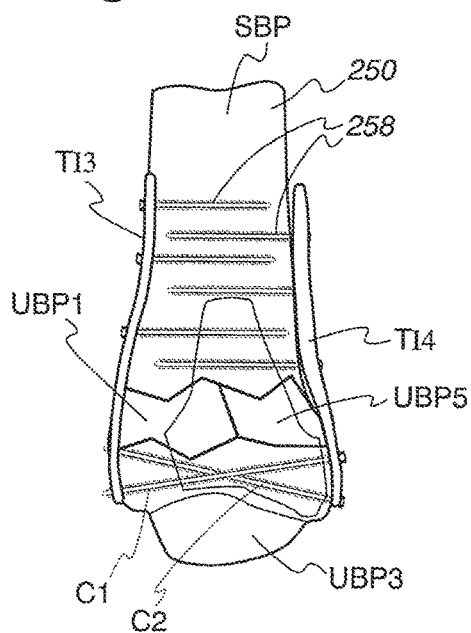
FIG. 47 is a view of the components as in FIG. 45 but taken from the lateral side.

In FIGS. 45-47, implants TI3, TI4 and TI5, TI6 are paired respectively at lateral and medial locations on the anterior and posterior surfaces of the distal tibia 250 that is fractured so as to produce a stable bone part SBP and unstable bone parts UBP1-UBP5. The implant pairs are substantially the same in terms of their basic function, with exemplary implant pair TI3, TI4 described hereinbelow.

The implants TI3, TI4 are mounted in spaced relationship to each other and conform to a respective tibia surface portion. The implants TI3, TI4 are each designed to use either or both of two components C1, C2, corresponding to the component C in FIG. 44. However, the multiple component arrangement is not required. By crossing the components C1, C2, as in the "X" shape shown, additional stability is afforded. Each of the components C1, C2 has opposite ends, connected one each to the implants TI3, TI4, using any of the structures described above.

Fixation elements 258 fix the implants TI3, TI4 to the stable bone part SBP. With the tibia 250 fractured as shown, the components C1, C2 extend only through the unstable bone parts UBP1-UBP5.

Figure 48:
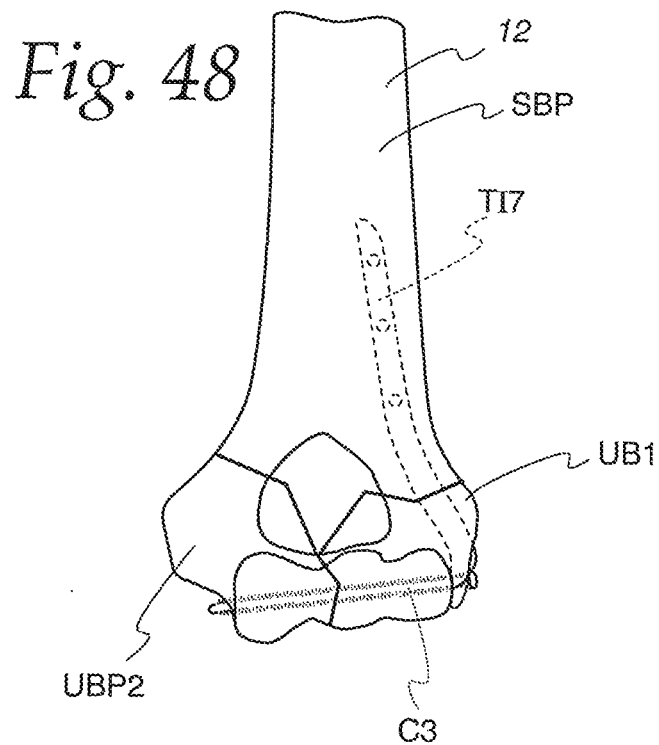
FIG. 48 is a fragmentary, elevation view of a distal humerus region with a single intramedullary implant according to the invention at a lateral location.

In a further embodiment, as shown in FIG. 48, a single, intramedullary implant TI7 is shown on a tibia 250 at a lateral location to accept a threaded component C3 to stabilize unstable bone parts UBP1, UBP2 in relation to a stable bone part SBP.

Figure 49:
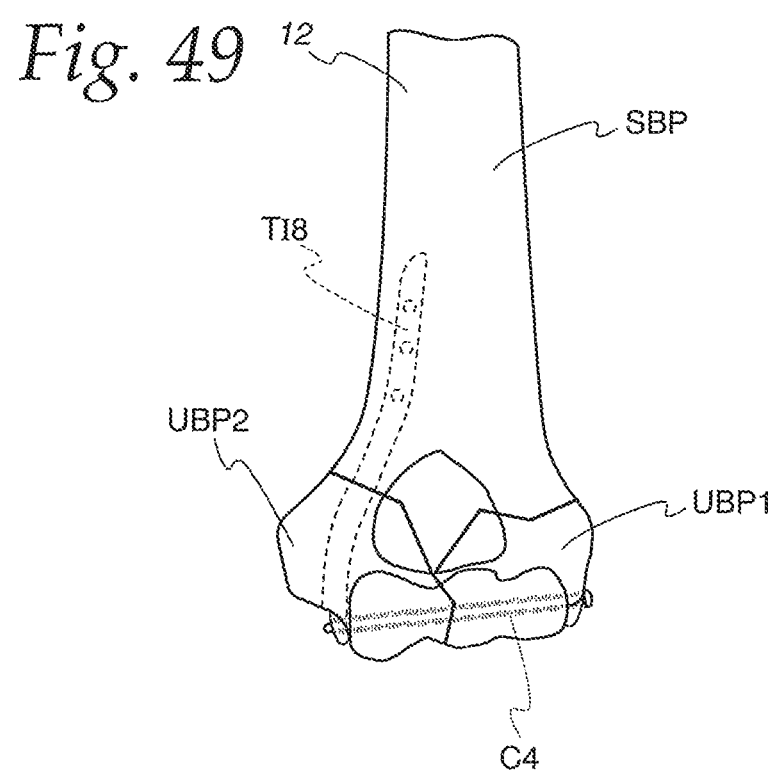
FIG. 49 is a view as in FIG. 48 wherein the intramedullary implant is at a medial location.

FIG. 49 shows an arrangement similar to that in FIG. 48 but with the single, intramedullary implant I8 located at a medial location on a tibia 250 fractured to produce unstable bone parts UBP1, UBP2 separated from a stable bone part SBP. A threaded component C4 extends into the implant TI8 and each of the unstable bone parts UBP1. UBP2.

In FIGS. 50-53, a modified and preferred form of implant, corresponding to the implant 120, described above, is shown at 120'. Corresponding parts are identified with the same reference numeral, with the parts identified in FIGS. 50-52 including a "'" designation.

The implant 120' has an elongate body 121' with an intramedullary portion 122' having a length between a first end 258 and a distal second end 123' at which a paddle 124' is located and mounted in cantilever fashion. The implant 120' is configured for use at a medial location at the distal humerus up into the canal and could be easily adapted for directing from a lateral location on the distal humerus up into the canal. Use on still other bones is contemplated.

The intramedullary portion 122' has a substantially constant dimension/diameter' D, as taken in cross-section transversely to the length of the implant 120', as indicated generally by the double-headed arrow 258. The paddle 124', and a bone engaging surface 260 thereon, have a dimension D1, extending transversely to the length of the implant 120', that is substantially greater than the dimension D. In this embodiment, the dimension D1 is approximately three times the dimension D. Preferably, the dimension D1 is at least two times the dimension D so that the portion of the paddle 124' projecting past the body 121' projects a distance D2 that is equal to or greater than the dimension D, to provide the desired stabilization of the implant 120' relative to the bone that is being treated. However, at certain sites, because of geometrical constraints, the dimension D1 may be the same as, or smaller than, the dimension D. In this embodiment, the paddle 124' projects in only one direction away from the intramedullary portion 122' to define an "L" shape in conjunction therewith.

In alternate forms, not specifically shown, the paddle may project in more than one direction away from the intramedullary portion so as to define a "Y" shape, a "T" shape, or another shape in conjunction therewith.

The paddle 124' and bone-engaging surface 260 thereon have a dimension D3, generally parallel to the lengthwise extent of the intramedullary portion 122', that is substantially greater than the dimension D; preferably on the order of at least twice that dimension, again for purposes of stability.

In this embodiment, the paddle 124' cantilevers from the second lengthwise end 262 of the intramedullary portion 122', to project transversely to the length of the intramedullary portion 122', and has an overall generally "U" shape opening towards the first end 258 of the implant 120' and intramedullary portion 122'

While the implant 120 has a somewhat different configuration than the implant 120', the general layout and relationship of parts, in both shape, orientation, and dimension, is generally similar with the overall function being the same.

The intramedullary portion 122' is made up of a primary length portion 266 and a second length portion 268. The length portions 266, 268 have lengthwise central axes 270, 272, respectively, that make an angle Θ with respect to each other. The angle Θ may be in the range of 5-15°. As depicted, the angle Θ is 9'.

A paddle support 274 projects from the second end 262 in a line L1 from the second axis 272 at the second end 262. The support 274 produces a cantilever mount for the paddle 124'.

The primary length portion 266 has a first length with the second length portion 268 having a second length. The first length is greater than the second length. In the depicted embodiment, the first length is less than twice the second length.

The paddle surface 260 has an area. Preferably, at least a portion of the surface area faces away from the axis 270. As depicted, substantially the entirety of the area is spaced from and faces away from the axis 270.

While the cantilever paddle mount is depicted to establish the relationship between the paddle surface 260 and axis 270, this same relationship could be produced without the cantilever design.

The surface 260 has separate, angled, first and second flat portions 276, 278 residing substantially in first and second planes that are at an angle Θ1 that is in the range of 165-172°. However, it should be understood that the paddle could be made without the angled surface portions.

The implant 120' has openings 280 to accept the fixation elements 128' that are directed in a line that is transverse to the length of the implant 120', potentially at different angles with respect thereto, as to avoid anatomical structures and/or to provide a biomechanical advantage.

The implant 120' is configured so that the implant end 264 can be introduced to the intramedullary canal/cavity and moved in a substantially straight line fully operatively therewith parallel to the length of the intramedullary portion 122' without requiring any significant angular reorientation of the implant 120'. Preferably, the operative placement of the implant 120' does not require any bending, or other reconfiguration, of the implant 120', and particularly the intramedullary portion 122'. The operatively placed implant 120' is then secured in the same general manner as described for the implant 120. The implant may be used as the sole implant or in conjunction with another implant, as described hereinabove.

The second length portion 268 has a peripheral surface on which a discrete undercut/recess 282 is formed to provide a clearance volume to avoid encroachment of the implant 120' upon adjacent anatomical parts. For example, in one application, the undercut/recess 282 avoids impingement in the olecranon fosse with the ulna as the elbow is extended. The recess 282 has a generally obround shape bounded by spaced, elongate edges 284, 286 that have lengths aligned with the length of the second length portion 268. The recess 282 extends over a majority of the lengthwise extent of the second length portion 268.

The paddle 124' is secured to the bone B using one or more fixation elements, such as screws/pins 126', for which suitable openings/bores are preferably pre-formed.

The implant 120' is particularly adaptable to facilitating setting of fractures on the distal humerus or distal femur, but is not so limited and could be used as depicted, or modified for use at other sites.

In one application, it may be desirable to have the bone engaging surface of the paddle arranged so that at least a portion of the bone engaging paddle surface: a) is in line with an axis that is parallel to the central axis of the intramedullary portion; and b) intersects a substantial length of the intramedullary portion. That is, an extension of the diameter of the intramedullary portion would intersect at least a portion of the bone engaging paddle surface. The paddle in this arrangement may be mounted other than by using a cantilevered support.

With the structure as described above, a method of treating fracture of a bone with an intramedullary canal can be carried out as showed in flow diagram form in FIG. 53. As shown at block 288, therein, a system is provided, as described above. As shown at block 290, the intramedullary portion of the first implant is directed into the intramedullary canal to place the first implant into an operative position. As shown at block 292, the operatively positioned first implant is secured to the bone.

In FIG. 54, a system is schematically depicted for treating a fracture of a bone 300 with an intramedullary canal 302. The fracture produces first and second bone parts separated by a fracture line.

The system includes a first implant 304 with an elongate body 306 configured to be directed into the intramedullary canal 302 to place the first implant 304 in an operative position on the bone 300. At least a first fixation component 308 can be advanced into the bone 300 and into the elongate body 306 with the first implant 304 in the operative position.

The system in FIG. 54 is shown schematically to encompass a system as shown in FIGS. 18-22, other embodiments described herein, and further variations. The first implant 304 corresponds to the implant 120, with the main difference relating to openings 310 in the body 306, corresponding to the openings 129 in the body 121. Of course, the configuration of the first implant 304 is not limited to the configuration shown in FIGS. 18-22. The fixation component(s) 308 encompasses the fixation components 128 shown in FIGS. 18-22, and variations thereof, such as those described herein.

One specific form of system, as shown generically in FIG. 54, is shown in FIG. 55. The fixation component 308 therein has a leading end 312 and a trailing end 314. The leading end 312 has a tip 316. The trailing end 314 has a first set of threads 318 to engage the bone 300 over a first lengthwise extent E of the first set of threads 318 with the fixation component 308 advanced in the direction of the arrow 320 into the bone 300 and elongate body 306 of the first implant and secured, as shown in FIG. 55. The fixation component 308 has a first length FL that advances into the elongate body 306, with the first implant 304 operatively positioned, as the fixation component 308 is advanced and secured.

The first length FL is capable of passing through a bore of a diameter that is less than a diameter of a bore required to pass through the first extent E of the first set of threads 318 that engages the bone 300.

In this embodiment, the first length FL is shown with a substantially uniform diameter, over substantially the entirety of its length, that is less than the diameter of at least a portion of the fixation component 308 over the portion thereof where the first extent of threads E is formed. A generic showing of these components is intended to encompass the specific forms shown and any other form whereby the first length FL is capable of passing through a bore with a diameter that is less than required to pass the first extent of the corresponding first set of threads 318. As one possible variation, the diameter of the first length of the fixation component 308 might be non-uniform. Essentially, the invention is intended to encompass a construction wherein at least some of the threads in the first set of threads 318, that engage the bone 300, have a diameter greater than that of the implant opening 310. This allows the implant opening 310 to be made relatively smaller to maintain the integrity of the implant 304.

In FIG. 55, the fixation component 308 is shown advanced fully through the elongate body 306. However, this is not a requirement, as the tip 316 may reside within the thickness of the implant body 306 between opposite sides 322, 324.

In this embodiment, no part of the first set of threads 318 is shown advanced into the opening 310. It is possible with a tapered configuration for the first set of threads 318 that a certain number of the threads might be advanced into the opening 310 without requiring a diameter larger than that required to closely accept an unthreaded portion 326 of the fixation component 308 that extends between the tip 316 and a lengthwise location at 328 where the first set of threads 318 begins. Alternatively, what is shown as the unthreaded portion 326 could have threads with a smaller diameter.

In FIG. 22, the corresponding fixation component 128 is shown to be advanced through the corresponding elongate body 121 to fully span the intramedullary canal and engage the bone at spaced locations. The fixation component 308 might be modified to similarly fully span the intramedullary canal.

The fixation component 308 has a second length between the tip 316 and the location 328 at which threads are formed. Alternatively, a second set of threads 330 may be provided over this corresponding length as shown on a modified form of fixation component 308' in FIG. 56. The second set of threads 330 may be provided to engage the bone 300 or the implant 304.

While the fixation component 308 is shown with a substantially uniform unthreaded diameter over a length between the tip 316 and location 328, the invention contemplates variations in diameter, such as a progressive or localized variation.

Preferably, the opening 310 in the implant 304 that accommodates the fixation component 308 has a diameter slightly larger than the diameter of the first length FL of the fixation component 308. This allows the first length FL to freely pass through the opening without resistance that might interfere with the surgeon's ability to readily insert the fixation component 308 during a procedure. As with the embodiment in FIGS. 18-22, it is contemplated that multiple openings 310 can be provided in the implant 304 to accommodate a corresponding number of fixation components 308.

It should be understood that "diameter", as used herein, is intended to encompass cross-sectional shapes that are not circular/round, or continuous at a peripheral surface thereof. Other shapes have an "effective diameter". The invention relates similarly to the effective diameters of the fixation components and openings.

The first set of threads 318 is shown with a tapering diameter. The invention also contemplates that corresponding threads 318", as shown on a fixation component 308" in FIG. 57, may have a uniform diameter over a length of the fixation component 308". The diameter of the set of threads 318" is greater than the diameter of the unthreaded portion of the fixation component 308" that is advanced into/through the implant opening 310.

In the depicted embodiment, the fixation component 308 is tapered and rounded at the tip 316 at the leading end 312 to facilitate advancing of the leading end 312 into and through the opening 310 in the implant 304.

With the system as described above, a method of treating a fracture of a bone can be carried out as shown in flow diagram form in FIG. 58.

As shown at block 332, a system is provided, of a type described above. As shown at block 334, the elongate body is directed into the intramedullary canal to place the implant into its operative position. As shown at block 336, a fixation component is advanced through the bone on at least one of two sides of the intramedullary canal and into the elongate body so that the first set of threads engages the bone at the one side.

A jig/guide can be utilized to drill aligned holes in the bone to accept the fixation component(s).

The invention contemplates that all embodiments herein could be adapted to treat a fracture of any bone that produces at least one unstable bone part adjacent to a stable bone part.

As described herein, the interaction of the first components and implants may be different in terms of how relative movement therebetween is confined. The first component may be blocked in movement in one or more directions/dimensions by the implant without being locked thereto. "Locking" may occur when the interacting parts thereof fix the interacting parts against relative; a) movement, in one or more different ways. For example, the parts may be locked against relative movement parallel to the length of the first component; b) angular movement; c) movement within a plane transverse to the length of the first component, etc. The locking could be a fixed locking against any relative movement.

The foregoing disclosure of specific embodiments is intended to be illustrative of the broad concepts comprehended by the invention. While much of the discussion has been described with fractures of the distal humerus, this is only by example and it is obvious to one skilled in the art that application to other areas such as pilon fractures of the distal tibia, plateau fractures of the proximal tibia, supracondylar fractures of the distal femur, or other sites would lend themselves to the principles of this invention.

The invention claimed is:

1. A method for treating a fracture of one of a tibial and humerus bone each with a length, the fracture producing first and second bone parts separated by a fracture line, the method comprising the steps of:

placing a first implant having a first body in an operative position against the one bone at one location, the first body elongate and having a length and at least a portion that overlies and conforms to an exposed outer surface of the one bone with the first body in the operative position, the length of the first body aligned with the length of the one of the tibial and humerus bone with the first body in the operative position;

placing a second implant having a second body in an operative position against the one bone at another location spaced from the one location, the second body elongate and having a length and at least a portion that conforms to an exposed outer surface of the one bone with the second body in the operative position, the length of the second body aligned with the length of the one of the tibial and humerus bone with the second body in the operative position;

directing a first elongate component through the one bone to cooperate with each of the first and second bodies so that the first and second bodies and first component together act to maintain the first and second bone parts in a desired set relationship, the first component having a lengthwise axis and cooperating with the first body so that the operatively positioned first component is stabilized by the first body in a first plane that is transverse to the lengthwise axis of the first component, the first component cooperating with the second body so that the first component is stabilized by the operatively positioned second body; and causing cooperating locking components on the first component and one of the first and second bodies to interact and lock the first component against movement relative to the one of the first and second bodies with the first component in its operative position.

2. The method for treating a fracture of one of a tibial and humerus bone according to claim 1 wherein the first component cooperates with the second body so that the first component is stabilized by the second body in a second plane that is transverse to the lengthwise axis of the first component.

3. The method for treating a fracture of one of a tibial and humerus bone according to claim 1 wherein the first component has first and second ends that engage the operatively positioned first and second bodies respectively at first and second locations so that the first and second ends of the first component are substantially fixed against movement relative to each of the first and second bodies in a direction transverse to the lengthwise axis at the first component.

4. The method for treating a fracture of one of a tibial and humerus bone according to claim 3 wherein the method further comprises the steps of using at least a first fixation element to fix the first body to the one bone at a location spaced from the first location and using at least a second fixation element to fix the second body to the one bone at a location spaced from the second location.

5. The method for treating a fracture of one of a tibial and humerus bone according to claim 4 wherein the at least first fixation element is in the form of a pin or a screw.

6. The method for treating a fracture of one of a tibial and humerus bone according to claim 4 wherein the at least second fixation element is in the form of a pin or a screw.

7. The method for treating a fracture of one of a tibial and humerus bone according to claim 1 wherein the first and second bodies each has first and second lengthwise ends, one of the first and second bone parts is a stable bone part and the other of the first and second bone parts is an unstable bone part, the method further including the step of fixing the first ends of the first and second bodies to the stable bone part each by at least one fixation element to maintain the first and second bodies operatively positioned, wherein the lengthwise axis of the first component is at an angle with respect to the lengths of each of the operatively positioned first and second bodies so as to extend through the unstable bone part.

8. The method for treating a fracture of one of a tibial and humerus bone according to claim 1 wherein substantially an entirety of the length of the first body is configured to conform to the exposed surface of the one bone.

9. The method for treating a fracture of one of a tibial and humerus bone according to claim 8 wherein the second body has at least one opening therein and further comprising the steps of obtaining a jig and engaging the jig with the second body to facilitate formation of a bore in the one bone that aligns with the opening in the second body.

10. The method for treating a fracture of one of a tibial and humerus bone according to claim 9 wherein the first and second bodies and first component are configured so that with the first and second bodies and first component operatively positioned the first and second bone parts reside captively between the first and second bodies.

11. The method for treating a fracture of one of a tibial and humerus bone according to claim 1 wherein the cooperating locking components are cooperating threads.

12. The method for treating a fracture of one of a tibial and humerus bone according to claim 1 wherein the cooperating locking components lock the first component relative to the one of the first and second bodies at a selected angular orientation from within a range of permitted angular orientations.

13. The method for treating a fracture of one of a tibial and humerus bone according to claim 1 wherein there are cooperating locking components on the first component and each of the first and second bodies that interact and lock the first component relative to each of the first and second bodies at selected angular orientations from within a range of angular orientations.

14. The method for treating a fracture of one of a tibial and humerus bone according to claim 1 wherein the first component has spaced first and second ends and there are first cooperating locking components on the first end of the first component and first body and second cooperating locking components on the second end of the first component and second body, and the method further comprises the steps of causing the first and second bodies and first component to be operatively positioned wherein the first and second cooperating locking components interlock and lock the first and second ends of the first component substantially against movement relative to the first and second bodies.

15. The method for treating a fracture of one of a tibial and humerus bone according to claim 14 wherein the first component has a body with a stepped diameter with smaller and larger diameter lengths.

16. The method for treating a fracture of one of a tibial and humerus bone according to claim 15 wherein the smaller and larger diameter lengths are both threaded to define the first and second locking components on the first component.

17. The method for treating a fracture of one of a tibial and humerus bone according to claim 1 wherein the first component has an end that extends into one of the first and second bodies without being locked to the one of the first and second bodies with the first and second bodies and first component operatively positioned.

18. The method for treating a fracture of one of a tibial and humerus bone according to claim 1 further including the steps of obtaining a jig and engaging the jig with each of the first and second bodies to facilitate formation of a bore for the first component.

19. The method for treating a fracture of one of a tibial and humerus bone according to claim 1 wherein the first body has a curved body part and a paddle shape on the curved body part.

20. The method for treating a fracture of one of a tibial and humerus bone according to claim 1 wherein each of the first and second bodies is configured to conform over substantially its entire length to an exposed surface on the one bone with the first and second bodies operatively positioned.

21. A method for treating a fracture of one of a tibial and humerus bone, the fracture producing first and second bone parts separated by a fracture line, the method comprising the steps of:
placing a first implant having a first body in an operative position against the one bone at one location,
the first body having at least a portion that overlies and conforms to an exposed outer surface of the one bone with the first body in the operative position;
placing a second implant having a second body in an operative position against the one bone at another location spaced from the one location and so that at least a part of the second body is within an intramedullary cavity of the one bone,
the second body having at least a portion that conforms to an exposed outer surface of the one bone with the second body in the operative position; and
directing a first elongate component through the one bone to cooperate with each of the first and second bodies so that the first and second bodies and first component together act to maintain the first and second bone parts in a desired set relationship, the first component having a lengthwise axis and cooperating with the first body so that the operatively positioned first component is stabilized by the first body in a first plane that is transverse to the lengthwise axis of the first component, the first component cooperating with the second body so that the first component is stabilized by the operatively positioned second body.

22. The method for treating a fracture of one of a tibial and humerus bone according to claim 21 wherein the portion of the second body projects from the intramedullary cavity with the second body operatively positioned.

23. The method for treating a fracture of one of a tibial and humerus bone according to claim 22 wherein the portion of the second body has a shape that is configured to conform to an exposed surface of a humerus at one of a lateral condyle region and a medial epicondyle region on the humerus.

24. The method for treating a fracture of one of a tibial and humerus bone according to claim 22 wherein the portion of the second body has a paddle shape.

25. The method for treating a fracture of one of a tibial and humerus bone according to claim 21 further comprising a fixation element that extends fully through the second body.

26. The method for treating a fracture of one of a tibial and humerus bone according to claim 25 wherein the fixation element has an unthreaded length that extends through the second body.

27. The method for treating a fracture of one of a tibial and humerus bone according to claim 26 wherein the fixation element has an entry end and a head end, the head end is threaded and the entry end is unthreaded.

28. A method of treating a fracture of a bone that produces first and second bone parts separated by a fracture line, the method comprising the steps of:

obtaining a system comprising a first implant having a first body to be placed in an operative position against the bone at one location;

a second implant having a second body to be placed in an operative position against the bone at another location spaced from the one location;

a first elongate component configured to be directed through the bone to cooperate with each of the first and second bodies so that the first and second bodies and first component together act to maintain the first and second bone parts in a desired set relationship, the first component having a lengthwise axis and cooperating with the first body so that the operatively positioned first component is stabilized by the first body in a first plane that is transverse to the lengthwise axis of the first component, the first component cooperating with the second body so that the first component is stabilized by the operatively positioned second body;

fixing the first body in its operative position against the bone;

fixing the second body in its operative position against the bone; and placing the first component in an operative position by directing the first component through the bone and supportingly against each of the first and second bodies respectively at first and second engaged locations so that the first component is thereby stabilized by the first and second bodies, wherein the step of placing the first component in an operative position comprises selecting a spacing between the first and second engagement locations from within a permitted range of spacing as dictated by a size and configuration of the bone, wherein the first component and first and second bodies are configured to allow the first component to be placed in a selected angular relationship with each of the first and second bodies within a range of angular relationships permitted between the first component and the first and second bodies.

29. The method for treating a fracture of a bone according to claim 28 wherein the first and second bodies are fixed in their operative positions before the first component is placed in its operative position.

30. The method for treating a fracture of a bone according to claim 28 wherein at least one of the first and second bodies is fixed in its operative position after the first component is placed in its operative position.

31. The method of treating a fracture of a bone according to claim 28 wherein the step of fixing the first body comprises using at least a first fixation element to fix the first body to the bone.

32. The method of treating a fracture of a bone according to claim 31 wherein the step of fixing the second body comprises using at least a second fixation element to fix the second body to the bone.

33. The method of treating a fracture of a bone according to claim 28 wherein the first component has first and second ends and the step of obtaining a system comprises obtaining a system wherein the first and second bodies each is elongate with a length between spaced first and second ends, the lengths of the operatively positioned first and second bodies are nominally aligned and the first end of the first component cooperates with the first body so that the first end of the first component and operatively fixed first body are substantially fixed against relative movement in a first line that is substantially parallel to the length of the first body.

34. The method of treating a fracture of a bone according to claim 33 wherein the second end of the first component and the second body cooperate so that the second end of the first component and operatively fixed second body are substantially fixed against relative movement in a second line that is substantially parallel to the length of the second body.

35. The method of treating a fracture of a bone according to claim 34 wherein the bone has a length that is at least nominally aligned with the lengths of each of the first and second bodies.

36. The method of treating a fracture of a bone according to claim 28 wherein one of the first and second bone parts is an unstable bone part and the first component extends into the unstable bone part.

37. The method of treating a fracture of a bone according to claim 36 wherein the other of the first and second bone parts is a stable bone part and the first component extends into the stable bone part.

38. The method of treating a fracture according to claim 28, wherein the step of fixing the first body in its operative position comprises fixing the first body against an outside surface of the bone.

39. The method of treating a fracture according to claim 38 wherein the step of fixing the second body in an operative position comprises directing the second body into an intramedullary cavity on the bone.

40. A method of treating a fracture of a bone that produces first and second bone parts separated by a fracture line, the method comprising the steps of:

obtaining a system comprising a first implant having a first body to be placed in an operative position against the bone at one location, a second implant having a second body to be placed in an operative position against the bone at another location spaced from the one location, and a first elongate component configured to be directed through the bone to cooperate with each of the first and second bodies so that the first and second bodies and first component together act to maintain the first and second bone parts in a desired set relationship, the first component having a lengthwise axis and cooperating with the first body so that the operatively positioned first component is stabilized by the first body in a first plane that is transverse to the lengthwise axis of the first component, the first component cooperating with the second body so that the first component is stabilized by the operatively positioned second body;

fixing the first body in its operative position against the bone;

fixing the second body in its operative position against the bone; and placing the first component in an operative position by directing the first component through the bone and supportingly against each of the first and second bodies, wherein the step of fixing the first body in its operative position comprises fixing the first body against an outside surface of the bone, wherein the step of fixing the second body in an operative position comprises directing the second body into an intramedullary cavity on the bone, wherein the second body has an exposed portion that projects from the intramedullary cavity on the bone and the step of placing the first component in an operative position comprises extending the first component between the first body and the exposed portion of the second body.

41. A method of treating a fracture of a bone that produces first and second bone parts separated by a fracture line, the method comprising the steps of:

providing a system comprising a first implant having a first body to be placed in an operative position against the bone at one location;

a second implant having a second body to be placed in an operative position against the bone at another location spaced from the one location;

a first elongate component configured to be directed through the bone to cooperate with each of the first and second bodies so that the first and second bodies and first component together act to maintain the first and second bone parts in a desired set relationship, the first component having a lengthwise axis and cooperating with the first body so that the operatively positioned first component is stabilized by the first body in a first plane that is transverse to the lengthwise axis of the first component, the first component cooperating with the second body so that the first component is stabilized by the operatively positioned second body;

fixing the first body in its operative position against the bone;

fixing the second body in its operative position against the bone; and placing the first component in an operative position by directing the first component through the bone and supportingly against each of the first and second bodies respectively at first and second engaged locations so that the first component is thereby stabilized by the first and second bodies, wherein the step of placing the first component in an operative position comprises selecting a spacing between the first and second engagement locations from within a permitted range of spacing as dictated by a size and configuration of the bone, wherein the first component and first and second bodies are configured to allow the first component to be placed in a selected angular relationship with the first and second bodies within a range of angular relationships permitted between the first component and the first and second bodies, wherein the bone is one of a tibial bone and a humerus bone and the first component engages each of the first and second bodies at portions where the first and second bodies are exposed at an outside surface of the one bone.

42. A system for treating a fracture of an elongate bone with a length, the fracture producing first and second bone parts separated by a fracture line, the system comprising:

a first implant having a first elongate body with a length to be placed in an operative position against the bone at one location;

a second implant having a second elongate body with a length to be placed in an operative position against the bone at another location spaced from the one location; and a first elongate component that can be directed into the bone to cooperate with each of the first and second bodies so that the first and second bodies and first component together act to maintain the first and second bone parts in a desired set relationship, the first component having a lengthwise axis and cooperating with the first body so that the operatively positioned first component is stabilized by the first body in a first plane that is transverse to the lengthwise axis of the first component at a selected angle in relationship to the first body within a range of angular relationships permitted between the first component and first body, the first component cooperating with the second body so that the first component is stabilized by the operatively positioned second body, wherein the first body is configured to conform to an exposed surface of one of a tibial bone and a humerus bone each with a length, with the lengths of the first body and one of the tibial bone and humerus bone aligned, wherein the second body is configured to conform to an exposed surface of the one of the tibial and humerus bone with the lengths of the second body and one of the tibial bone and humerus bone aligned.

43. A system for treating a fracture of a bone, the fracture producing first and second bone parts separated by a fracture line, the system comprising:

a first implant having a first body to be placed in an operative position against the bone at one location;

a second implant having a second body to be placed in an operative position against the bone at another location spaced from the one location;

each of the first and second bodies having at least a portion that is configured to overlie and conform to an exposed surface of the bone;

a first elongate component that can be directed through the bone to cooperate with each of the first and second bodies so that the first and second bodies and first component together act to maintain the first and second bone parts in a desired set relationship, the first component having a lengthwise axis and cooperating with the first body so that the operatively positioned first component is stabilized by the first body in a first plane that is transverse to the lengthwise axis of the first component, the first component cooperating with the second body so that the first component is stabilized by the operatively positioned second body; and a second elongate component that can be directed through the bone, extended between the first and second bodies, and connected to each of the first and second bodies to be stabilized by the first and second bodies, wherein the first component and first and second bodies are configured to allow the first component to be placed in a selected angular relationship with each of the first and second bodies within a range of angular relationships permitted between the first component and the first and second bodies.

44. The system for treating a fracture of a bone according to claim 43 wherein the second component has a lengthwise axis and the lengthwise axes of the first and second components are non-parallel to each other.

45. A system for treating a fracture of a bone, the fracture producing first and second bone parts separated by a fracture line, the system comprising:

a first implant having a first body to be placed in an operative position against the bone at one location;

a second implant having a second body to be placed in an operative position against the bone at another location spaced from the one location; and a first elongate component configured to be directed through the bone to cooperate with each of the first and second bodies so that the first and second bodies and first component together act to maintain the first and second bone parts in a desired set relationship, the first component having a lengthwise axis and cooperating with the first body so that the operatively positioned first component is stabilized by the first body in a first plane that is transverse to the lengthwise axis of the first component, the first component cooperating with the second body so that the first component is stabilized by the operatively positioned second body, wherein there are cooperating locking components on the first component and each of the first and second bodies that interact and lock the first component relative to each of the first and second bodies at selected angular orientations within a permitted range of angular orientations.

46. The system for treating a fracture of a bone according to claim 45 wherein the cooperating locking components comprise threads on the first component and threads on each of the first and second bodies that cooperate with the threads on the first component.

47. A method of treating a fracture of an elongate bone with a length that produces first and second bone parts separated by a fracture line, the method comprising the steps of:

obtaining a system comprising a first implant having a first elongate body with a length to be placed in an operative position against the bone at one location;

a second implant having a second elongate body with a length to be placed in an operative position against the bone at another location spaced from the one location;

a first elongate component configured to be directed through the bone to cooperate with each of the first and second bodies so that the first and second bodies and first component together act to maintain the first and second bone parts in a desired set relationship, the first component having a lengthwise axis and cooperating with the first body so that the operatively positioned first component is stabilized by the first body in a first plane that is transverse to the lengthwise axis of the first component, the first component cooperating with the second body so that the first component is stabilized by the operatively positioned second body;

fixing the first body in its operative position against an exposed outside surface of the bone wherein the length of the first body aligns with the length of the bone;

fixing the second body in its operative position against an exposed outside surface of the bone wherein the length of the second body aligns with the length of the bone; and placing the first component in an operative position by directing the first component through the bone and supportingly against each of the first and second bodies, wherein one of the first and second bone parts is an unstable bone part and the first component extends into the unstable bone part, wherein the other of the first and second bone parts is a stable bone part and the first component extends into the stable bone part.

* * * * *